United States Patent
Burton

(10) Patent No.: US 9,532,127 B2
(45) Date of Patent: Dec. 27, 2016

(54) EARBUDS AND IN-EAR ADAPTER FOR EARBUDS

(71) Applicant: Burton Technologies, LLC, Ludington, MI (US)

(72) Inventor: John E. Burton, Ludington, MI (US)

(73) Assignee: Burton Technologies, LLC, Ludington, MI (US)

( * ) Notice: Subject to any disclaimer, the term of this patent is extended or adjusted under 35 U.S.C. 154(b) by 0 days.

(21) Appl. No.: 14/166,129

(22) Filed: Jan. 28, 2014

(65) Prior Publication Data

US 2014/0138179 A1 May 22, 2014

Related U.S. Application Data

(63) Continuation-in-part of application No. 12/178,172, filed on Jul. 23, 2008, now Pat. No. 8,638,970.

(60) Provisional application No. 61/019,357, filed on Jan. 7, 2008, provisional application No. 61/028,206, filed on Feb. 13, 2008.

(51) Int. Cl.
*H04R 1/10* (2006.01)
*H04R 25/00* (2006.01)
*A61F 11/08* (2006.01)

(52) U.S. Cl.
CPC ....... *H04R 1/1016* (2013.01); *A61F 2011/085* (2013.01); *H04R 25/656* (2013.01)

(58) Field of Classification Search
CPC ... H04R 1/1016; H04R 1/1058; H04R 1/2811; H04R 1/2803; H04R 1/10; H04R 1/1066; H04R 2460/09; H04R 2460/11; H04R 25/65; H04R 25/656; H04R 25/658
See application file for complete search history.

(56) References Cited

U.S. PATENT DOCUMENTS

| | | |
|---|---|---|
| 2,489,277 A | 9/1945 | Faralla |
| 2,487,038 A | 11/1949 | Baum |
| 2,508,918 A | 5/1950 | Hines, Jr. |
| 4,349,083 A | 9/1982 | Bennett |
| 4,677,679 A | 6/1987 | Killion |
| 4,763,753 A | 8/1988 | Killion |
| 4,852,683 A | 8/1989 | Killion |

(Continued)

OTHER PUBLICATIONS iBuds, AccessoryGeeks.com, published at least as early as Mar. 22, 2005.

(Continued)

*Primary Examiner* — Matthew Eason
(74) *Attorney, Agent, or Firm* — Warner Norcross & Judd LLP

(57) ABSTRACT

An earphone or adapter for attaching to an earphone includes an ear portion including a tubular sidewall. In one embodiment, the tubular sidewall includes an inner surface defining an air channel extending through the sidewall. The air channel redirects sound at an angle to the speaker axis, and may have a smooth contour to maintain sound quality. In one embodiment, the inner surface has a twin cone shape including a converging cone portion extending from the first end and a diverging cone portion extending from the converging cone portion to the second end. The outer surface of the tubular portion may include a plurality of outwardly extending fins In one embodiment, the tubular portion includes both a plurality of fins, and a twin cone air channel.

25 Claims, 40 Drawing Sheets

(56) References Cited

U.S. PATENT DOCUMENTS

| | | | |
|---|---|---|---|
| 5,113,967 | A | 5/1992 | Killion et al. |
| 5,319,163 | A | 6/1994 | Scott |
| 5,887,070 | A | 3/1999 | Iseberg et al. |
| 6,205,227 | B1 | 3/2001 | Mahoney et al. |
| 6,411,722 | B1 | 6/2002 | Wolf |
| RE38,351 | E | 12/2003 | Iseberg et al. |
| 6,666,295 | B2 | 12/2003 | Killion et al. |
| 6,724,902 | B1 | 4/2004 | Shennib et al. |
| 6,830,876 | B2 | 12/2004 | Killion et al. |
| 8,189,846 | B2 | 5/2012 | Tiscareno et al. |
| 8,270,656 | B2 | 9/2012 | Stiehl et al. |
| D681,015 | S | 4/2013 | Akana et al. |
| D691,594 | S | 10/2013 | Akana et al. |
| 8,731,228 | B2 | 5/2014 | Burgett |
| D707,206 | S | 6/2014 | Akana et al. |
| 2005/0141743 | A1 | 6/2005 | Seto |
| 2005/0147269 | A1* | 7/2005 | Oliveira et al. .............. 381/382 |
| 2007/0189569 | A1 | 8/2007 | Haapapuro et al. |
| 2007/0240931 | A1 | 10/2007 | Killion |
| 2008/0187159 | A1 | 8/2008 | Blanchard |
| 2009/0202097 | A1 | 8/2009 | Tiscareno |
| 2009/0316944 | A1 | 12/2009 | Tiscareno |
| 2010/0061583 | A1* | 3/2010 | Taenzer et al. ........ H04R 25/00 381/380 |
| 2014/0068944 | A1* | 3/2014 | Aase et al. ................... 29/896.2 |

OTHER PUBLICATIONS

The Whoomp! Earbud Enhancers Review: Apple's Dirty Little Secret, posted Apr. 18, 2008.
Griffin EarJams, iLounge, Jeremy Horwitz, published Sep. 14, 2004.
TuneBuds, Belkin, posted to website May 24, 2006.

\* cited by examiner

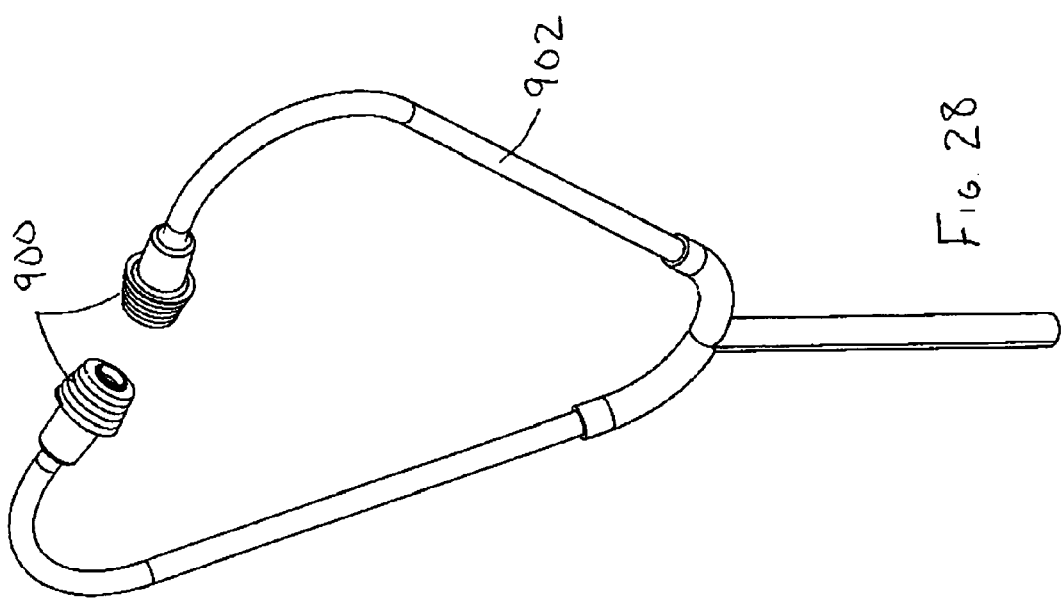

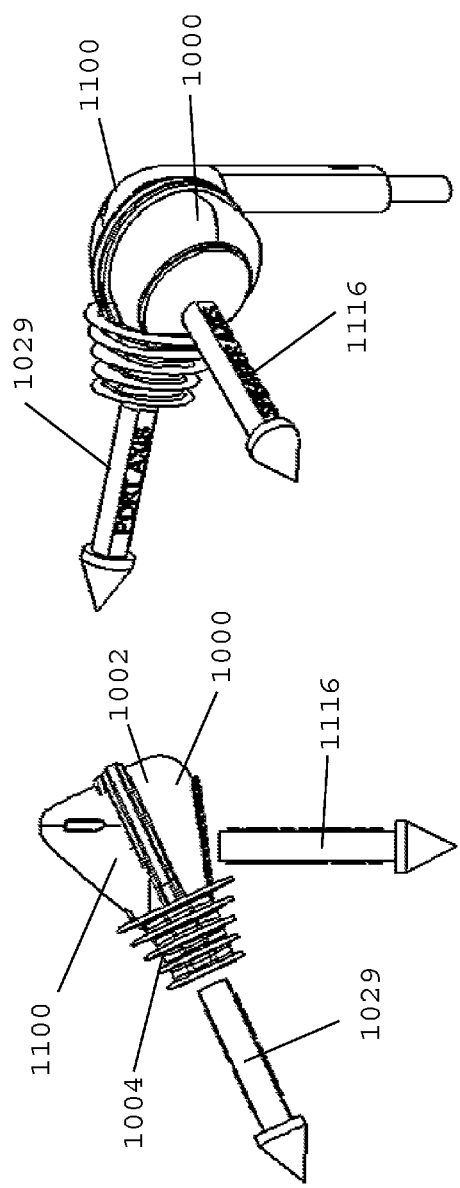
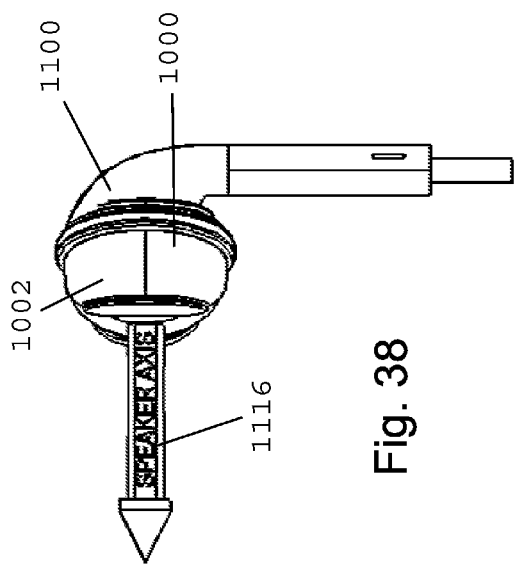
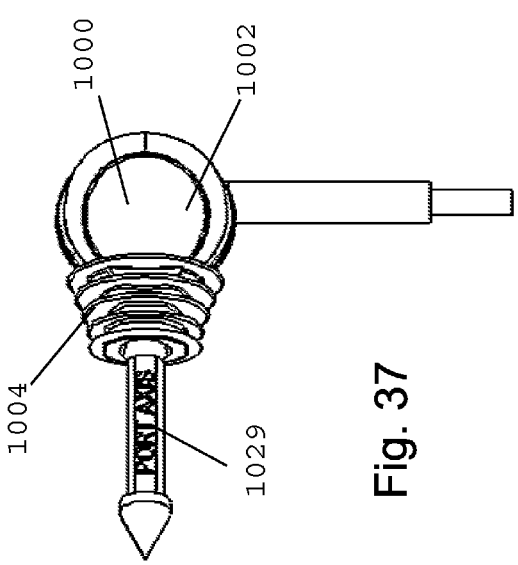
Fig. 35
Fig. 36
Fig. 37
Fig. 38

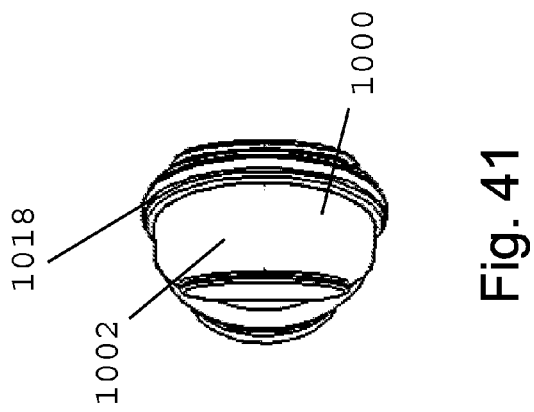
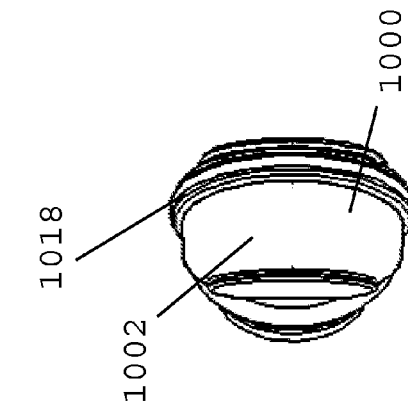
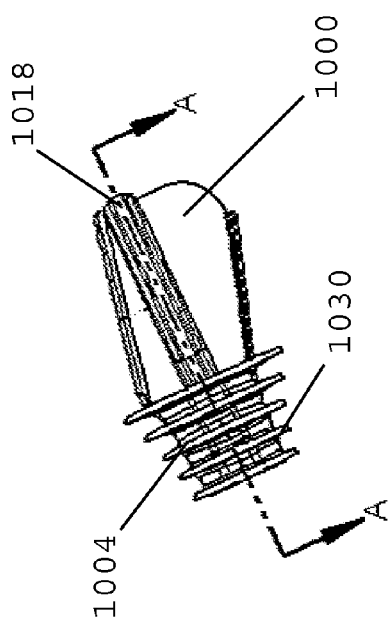
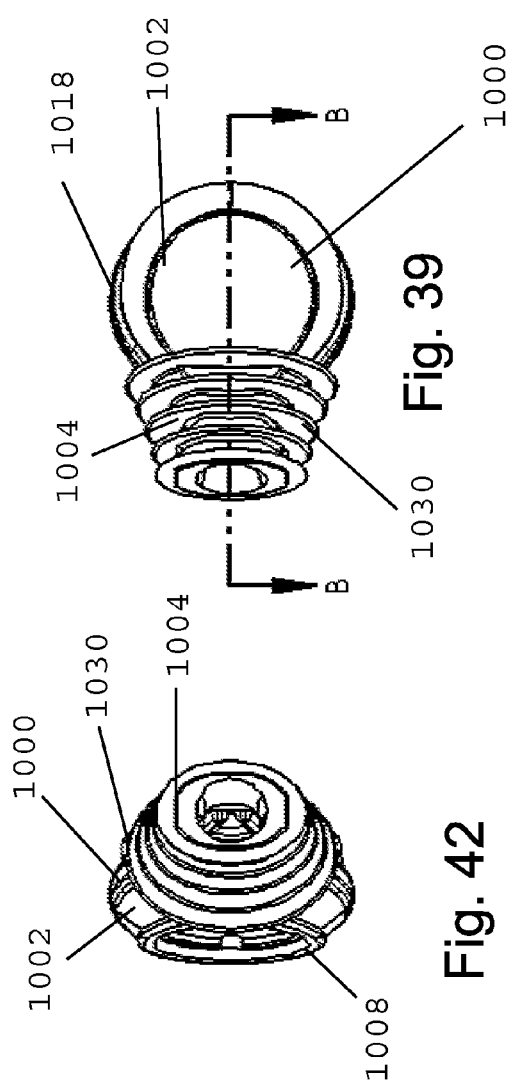

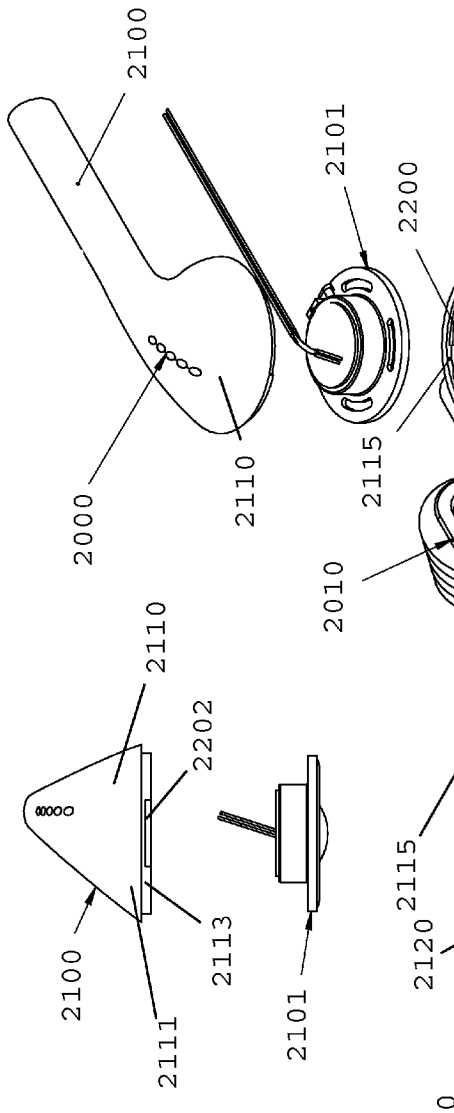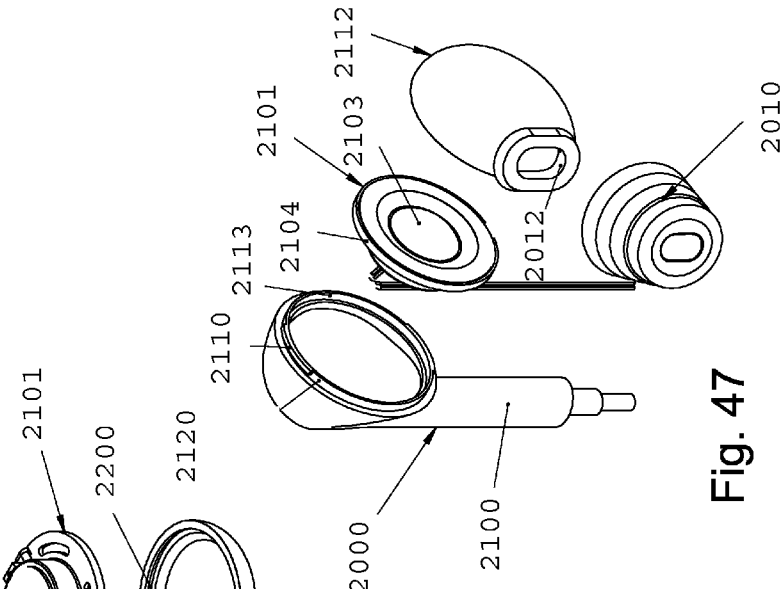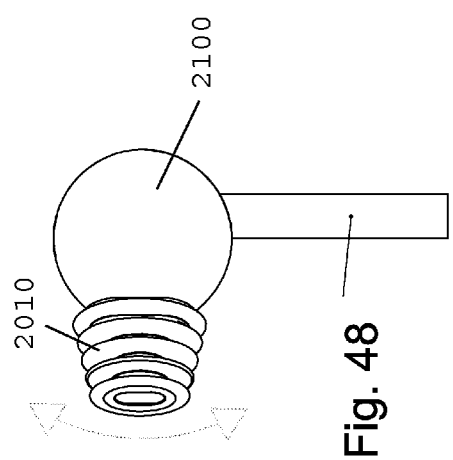

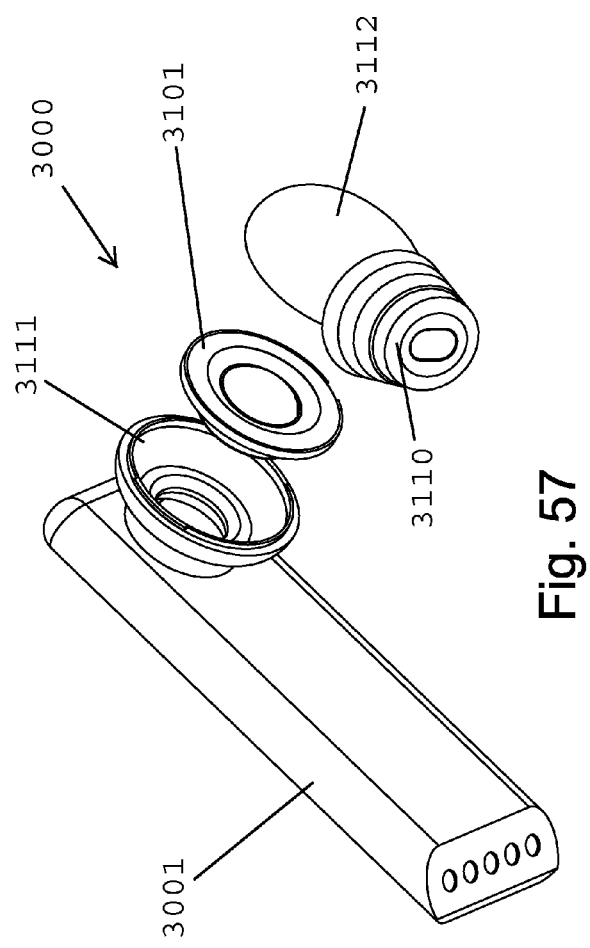
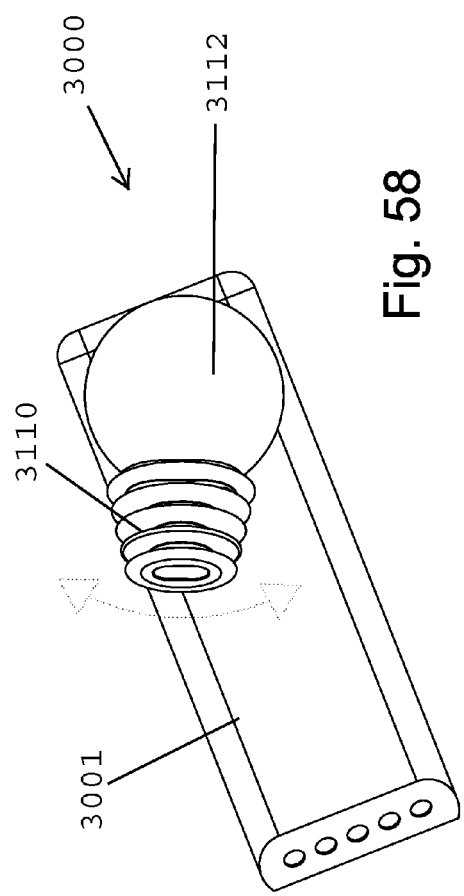

EARBUDS AND IN-EAR ADAPTER FOR EARBUDS

BACKGROUND OF INVENTION

The present invention relates generally to earphones, including variations known as "earpods" and "earbuds," for handheld electronic devices, such as portable media players ("PMP's") as well as hearing aids, cellular telephones, Bluetooth earpieces and other devices adapted for hearing. More particularly, the invention relates to an earphone and a flexible earphone adapter (also known as "tips", "covers" or "gels") that provides enhanced sound isolation, improves retention of the earphone inside the ear even under extreme activity and perspiration and minimizes acoustical impedance within the ear canal area.

PMP's are popular to use for listening to music while walking or running outdoors or inside on a treadmill, for example. They are commonly used with earbuds, which are miniature speakers that fit into the ears at the entry of the ear canal. Earbuds are comfortable and well suited for this use since they are pocket sized, lightweight and independent pieces that are not as cumbersome to wear or carry as headphones, which have a connecting framework. However, there are a number of drawbacks associated with earbuds. First, they are often ineffective at blocking out ambient noise and preventing leakage of the amplified sound into the surrounding area. Second, the position of the earbud in the ear is often not well controlled or aimed. The result is an erratically shaped passageway for the sound wave to travel as it leaves the speaker inside the earbud and makes its way into the ear canal. Abrupt changes in the direction or area of the passageway through which a sound pressure wave travels will alter both the pressure levels and the molecule motion within the pressure wave and distort the sound produced from the speaker. This type of interference of a sound pressure wave is often called "acoustical impedance" and is well known in the design of horns and wind instruments. Like electrical impedance often specified for speakers, acoustic impedance must be minimized for improved sound quality. The phenomenon of acoustical impedance is readily experienced by simply experimenting with different positions of the earbud within the ear. Third, many users find it difficult to keep the earbud retained in the ear. The cord extending from the earbud is easily snagged, and generally swings or bounces with activity. This movement, combined with perspiration in the ear, can often dislodge the earbud from the ear. In some cases, the earbud can become further entangled in exercise equipment or become an annoying distraction when the listener must repeatedly stop his or her activity to re-secure the earbud. Lastly, fitting the earbud to the ear needs to be accomplished without discomfort to the user. Some users feel discomfort due to the earbuds rigid circular shape which can create too much interference and pressure on the ear.

A number of attempts have been made to design earbuds and related accessories that address the basic problems of retention, the improvement of sound isolation and in ear comfort, but these designs are still significantly lacking in performance in one area or another. One attempt is a thin foam rubber cover that surrounds the earphone speaker area. The cover adds some grip to the area just outside the ear canal. However, this thin foam easily tears, does not provide improved sound isolation, and the increased grip is generally inadequate to retain the ear piece to the ear with increased levels of activity and motion.

Another attempt to improve retention is an ear piece design with a hook feature that encircles the back side of the ear. First, the hook feature adds considerable bulk to the earbud and is less convenient to carry. Also, the external shape and size of the of the ear in relation to the position, size and angle of entry of the ear canal vary greatly from individual to individual. As a result of the misalignment between speaker and ear canal, sound isolation is difficult to achieve and distortion caused by acoustic impedance becomes problematic.

Yet another attempt to improve retention is to provide earbuds with an "in-ear" elastomeric (often rubber) "insert" portion that fits inside at least a portion of the ear canal. This has the added advantage of improving sound isolation (as explained in more detail below). One existing insert shape that fits inside the ear canal includes a tapered cylinder with a smooth rubber outer surface that is attached to the ear piece by sliding the insert over a rigid tubular support that is formed with the earphone and extends outwardly from the speaker face. The tubular support allows the passage of sound from the speaker through its center, and its outer surface provides a support and attachment portion for the insert. In some cases, the in-ear insert portions are replaceable with small, medium and large sizes as options. Another insert design includes a spherically shaped hollow outer surface attached to the earbud with a hole through the center for the passage of sound. The spherically shaped design includes a mounting portion that fits onto the earbud over the speaker face.

All of the aforementioned in-ear methods still have drawbacks that cause inadequate retention of the ear piece to the ear canal. This is partly due to the fact that the ear canal has an irregular, non-circular cross section and that the axis or "path" of the ear canal is not linear but rather a circuitous path on its way to the ear drum. The cylindrical elastomeric insert designs described do not conform well to the path of the ear canal due to the rigid structure on which they are mounted. These elastomeric inserts conform less to the shape of the path of the ear canal but rather reshape the ear canal's path to become more the shape of the adapter. The result is a less than optimum fit within the ear canal area, uneven pressure exerted on the ear, and potential discomfort. In addition, because the contours of these elastomeric inserts do not match with the path of the ear canal, gaps can exist and the resiliency of the ear canal to return to its normal shape can act to push out and dislodge the earbud, especially with the help of perspiration and motion from exercise activity.

Another drawback of existing in-ear designs is the smooth surface of the elastomeric profile. When perspiration is introduced, the sweat can migrate into the ear canal and reduce friction by effectively becoming a layer of lubricant between the insert and the ear canal. A hydroplaning effect occurs with heavy perspiration, such that the slightest activity and movement can cause the insert and the earphone to become quickly dislodged.

Another drawback of existing in-ear designs is that the tubular support used for mounting the insert is poorly shaped to minimize acoustical impedance in that the sound pressure wave travels down a passageway that takes an abrupt change in area from the speaker diameter to the tube diameter and then another abrupt change from the tube diameter as it exists into the ear canal.

In addition to retaining the earphone in the ear, it is also highly desirable to block out noise from the surrounding environment or from the wind for better audio clarity. This is commonly called "sound isolation" and involves significantly reducing or eliminating air gaps that allow the ingress of outside noise into the ear. Sound isolation also helps reduce the stray audio from the ear buds that may be heard by others, and less volume is needed to hear the audio since it is not competing with outside noise. Using less volume has a direct impact on conserving electrical energy which in turn may extend the duration the battery remains sufficiently charged for use. Another benefit of sound isolation is to help prevent feedback between the earphone speaker and a microphone in the case of a hearing aid or cellular phone.

Unfortunately, due to the drawbacks noted above, existing earphone products do not provide a comfortable product that is sufficiently retained in place on the ear during physical activities with a desired level of sound isolation.

SUMMARY OF THE INVENTION

The present invention provides both an earphone and an earphone adapter with both improved retention and sound isolation.

In one embodiment, the adapter includes a sleeve capable of fitting around the sidewall of the earbud to retain the adapter on the earbud, and an ear portion including a tubular sidewall having a first end attached to the sleeve and a second end opposite the first end. The tubular sidewall includes an outer surface, and a plurality of fins extending outwardly from the outer surface around the circumference of the tubular sidewall. The outer surface of the ear portion and the fins are flexible to permit the ear portion to deform as it is inserted into the ear canal. The height, thickness, shape and spacing of the ribs may be proportioned to maximize the retention of the adapter in the ear, while maintaining sound isolation.

In another embodiment, the tubular sidewall includes an inner surface defining an air channel, or passageway, extending through the sidewall to permit the passage of air and sound waves directly through the adapter and into the ear canal. The inner surface may be shaped to minimize acoustical impedance as the sound pressure wave travels through this passageway. In one embodiment, the inner surface has a twin cone shape, including a converging cone portion extending from the first end and a diverging cone portion extending from the converging cone portion to the second end, to provide the desired acoustics. The shape of the inner surface may be tuned to provide a particular tonality.

The adapter may be formed integrally from a single piece, such as an elastomer, for ease of manufacture. In one embodiment, the adapter is formed with an angle between the sleeve portion and the ear portion to permit the user to rotate the adapter to various positions with respect to the earbud for enhanced comfort and retention.

In one embodiment, the present invention is well suited as an accessory for the popular original equipment earbuds that come standard with the most popular portable music players. The shape of the outer surface of the ear portion and the shape and proportions of the ribs may increase the retention and sound isolation of these standard earbuds. The shape of the inner surface of the ear portion may further enhance the desired acoustics of the earbuds.

In another embodiment, the present invention is configured as an accessory for an earpod style earphone. In these earpod style earphones, substantially all of the speaker surface is covered with a rigid cover and sound is directed through one or more sound ports located on a lateral side of the cover adjacent a peripheral edge of the cover. In such an embodiment, the adapter may include a sleeve portion having an open end for extending over the cover of the earpod, a closed end that seats on the outer surface of the cover and a peripheral edge adjacent to the peripheral edge of the earpod cover. The ear portion extends from the peripheral edge of the sleeve such that it can align with the sound port when attached to an earpod. The ear portion may be similar to the above noted ear portion, including a tubular sidewall having a first end attached to the peripheral edge of the sleeve and a second end opposite the first end.

In one embodiment, the closed end of the sleeve may include one or more projections extending from its interior surface. As a result, portions of the closed end of the sleeve are held at a standoff from the earpod cover to direct sound exiting the speaker to the peripherally located ear portion.

In another embodiment, the present invention includes an earphone with an integral adapter. The earphone may provide the above noted sound and comfort advantages of the earbud and earpod style adapters, while eliminating the need for a user to attach the adapter to an earphone. The earphone may be provided with a swivel feature, wherein the cover and ear portion are capable of swiveling with respect to the speaker portion to provide an even more user friendly experience.

The current embodiments of this invention are shown in the following detailed description and drawings. Other variations, such as (but not limited to) the attachment mechanisms of the adapter to the earbuds, variations in size, proportion, and inclusion or exclusion of the specific individual features are anticipated by the inventor and will be recognized from the description of the current embodiments.

BRIEF DESCRIPTION OF THE DRAWINGS

FIG. 28 is a perspective view of an in-ear adapter according to another embodiment of the present invention;

FIG. 35 is a side view of an earpod and earpod style adapter;

FIG. 36 is a front perspective view of an earpod and an earpod style adapter;

FIG. 37 is a top view of an earpod and an earpod style adapter;

FIG. 38 is a side view of an earpod and an earpod style adapter;

FIG. 39 is a top view of an earpod style adapter;

FIG. 40 is a side view of an earpod style adapter;

FIG. 41 is a rear view of an earpod style adapter;

FIG. 42 is a front view of an earpod style adapter;

FIG. 45 is a side exploded view of an earpod style earphone according to one embodiment;

FIG. 46 is a rear perspective exploded view thereof;

FIG. 47 is a front perspective exploded view thereof;

FIG. 48 is a front view thereof with an arrow indicating the direction of swiveling;

FIG. 57 is an exploded view of one embodiment of a Bluetooth device;

FIG. 58 is a perspective view thereof.

DETAILED DESCRIPTION OF THE CURRENT EMBODIMENTS

I. Overview

Figure 1:
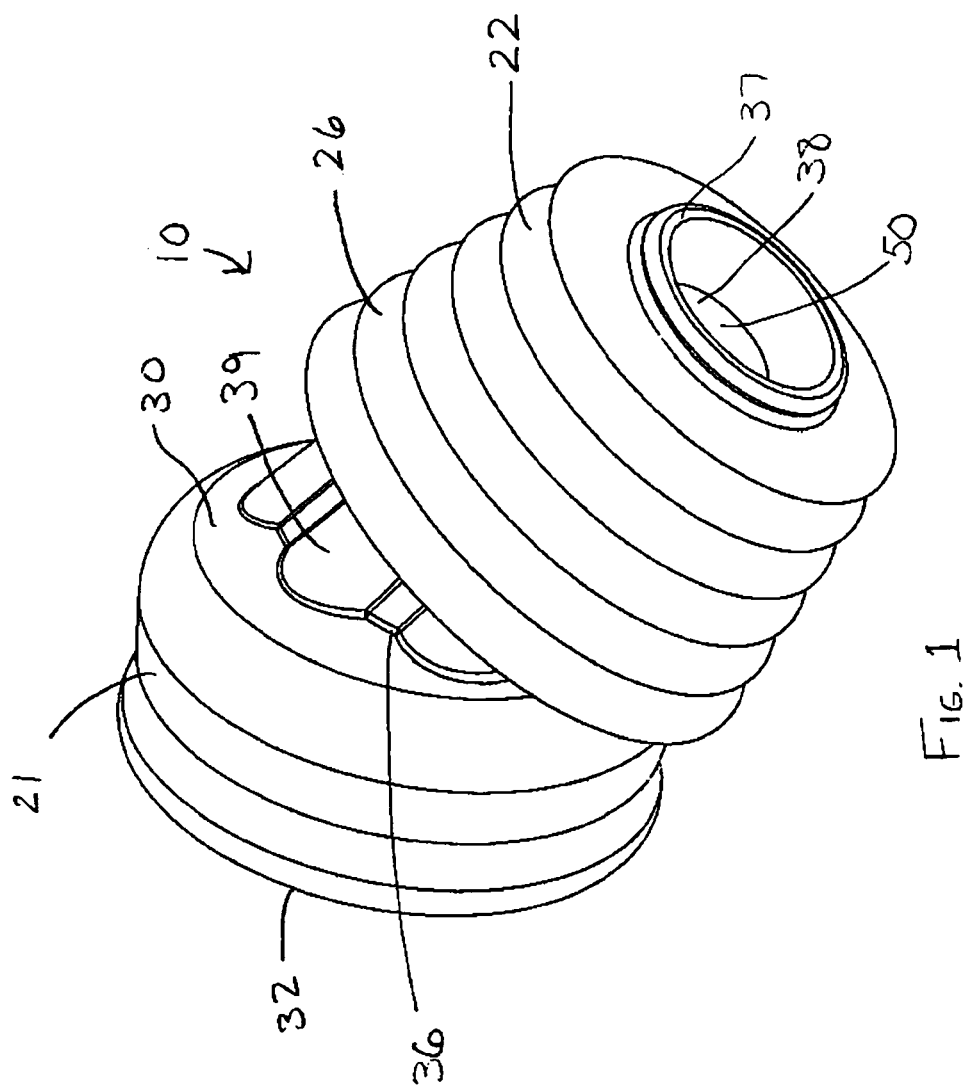
FIG. 1 is a perspective and exploded view of the in-ear adapter according to a first embodiment of the invention.

An in-ear adapter according to a first embodiment of the present invention is shown in FIG. 1 through FIG. 7 and is generally designated 10. As shown, the adapter 10 is designed to mount over an earphone or "earbud" 20 from an electronic component such as a portable media player, cellular telephone or hearing aid. For purposes of disclosure, the adapter 10 is described in connection with a particular earbud 100, shown in FIG. 8. The earbud 100 has a speaker housing 110 with a sidewall 111 that encapsulates the speaker, and a speaker port 112 mounted to a front edge of the sidewall 111. The speaker port 112 may include a hole or holes that permit the passage of sound through the speaker port 112.

As illustrated in FIGS. 1-7, the adapter 10 generally includes a sleeve portion 21 that attaches to the outside diameter of the earphone's sidewall 111, an ear portion 26 extending from the sleeve portion 21, and a plurality of fins 22 extending from the ear portion 26. In one embodiment, the adapter is made integrally, as a single, unitary piece from a soft elastomeric material such as silicone rubber, natural rubber or a thermoplastic elastomer (TPE) or another relatively soft, formable material, with a Shore A durometer of about 20 to 70, and in one embodiment about a 30 Shore A durometer. In another embodiment, wherein an even softer adapter is desired, the adapter may be made from a material such as a silicone rubber with a durometer between 5 and 20 Shore A. A variety of alternative materials are acceptable, depending of the desired application. For example, either foamed or solid rubber material would be suitable options. Alternative adapters may be made from two or more materials or pieces that are attached together to form the desired adapter shape.

II. Structure

Figure 4:
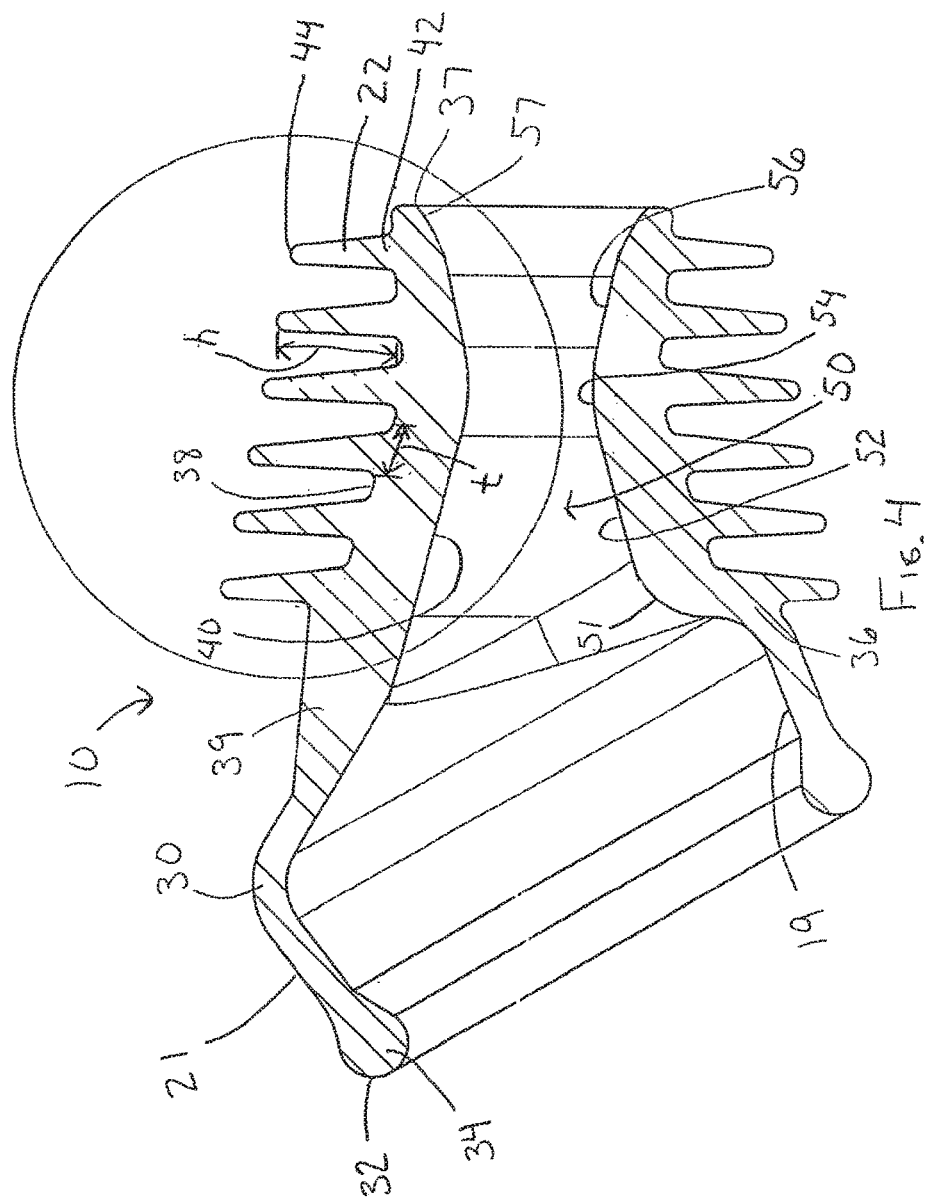
FIG. 4 is a side section view taken along line 4-4 in FIG. 3.
Figure 5:
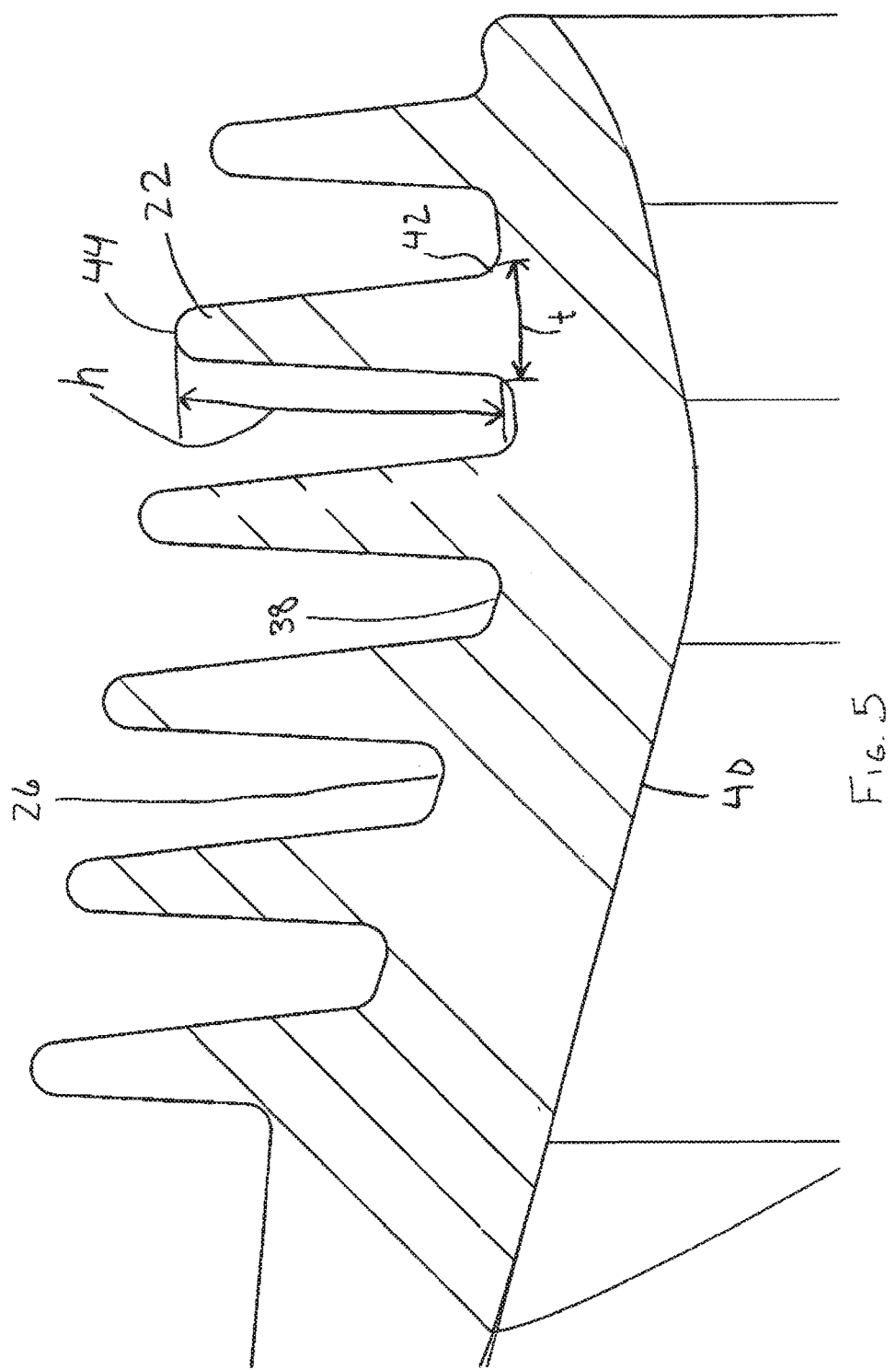
FIG. 5 is close-up view of the portion of the in-ear adapter circled in FIG. 4.
Figure 6:
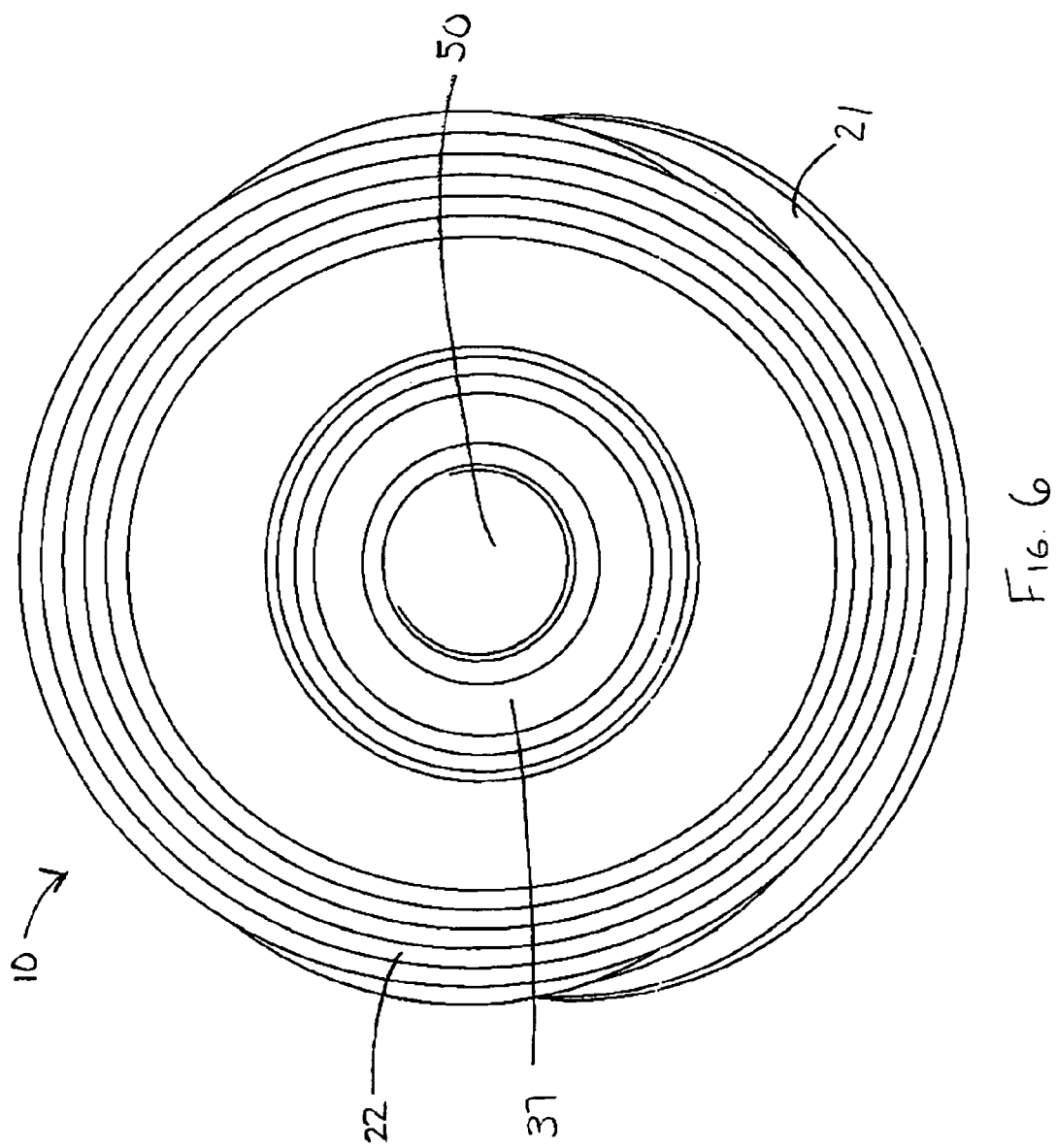
FIG. 6 is a front view of the in-ear adapter according to the first embodiment.
Figure 7:
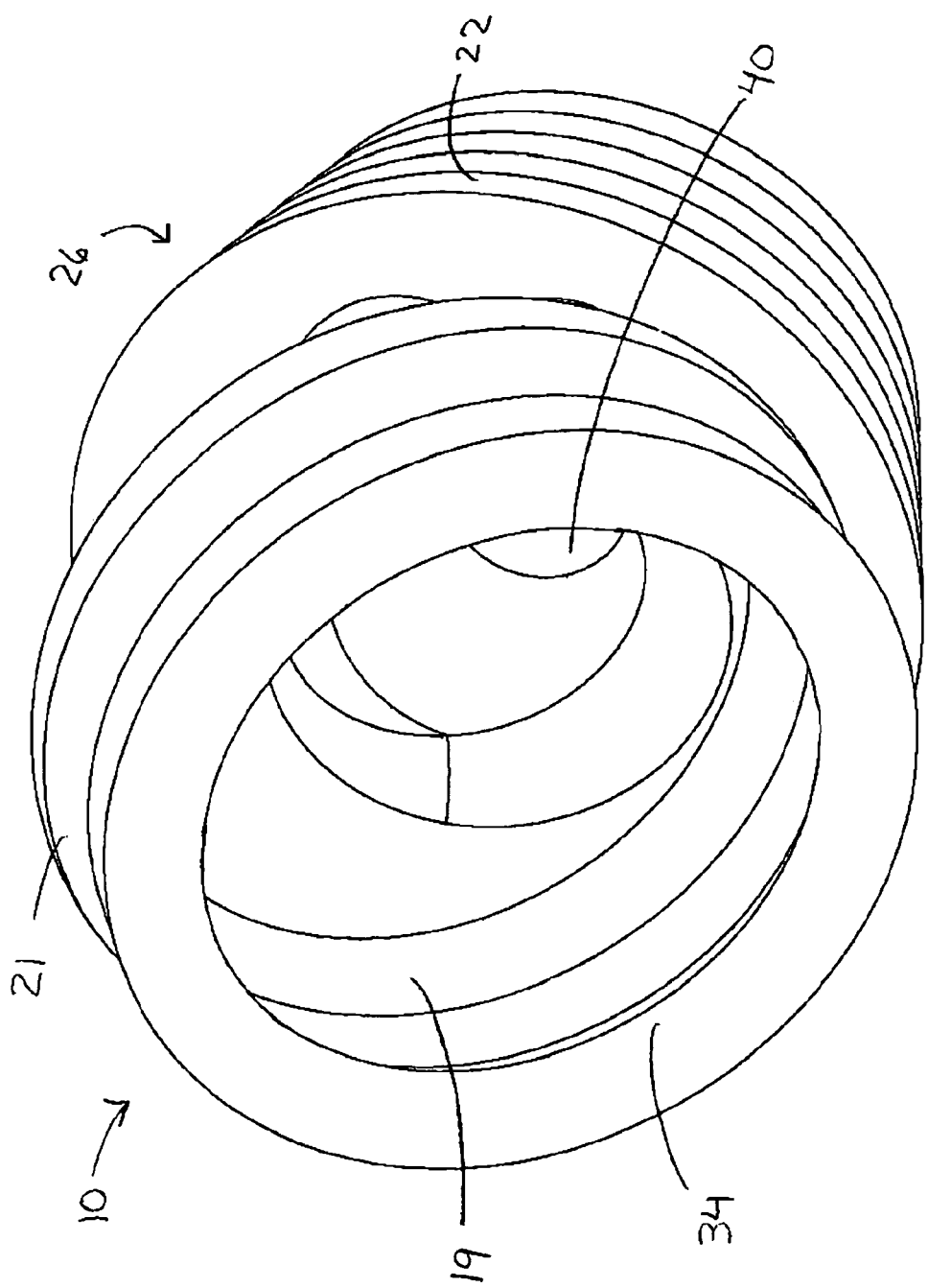
FIG. 7 is a rear perspective view of the in-ear adapter according to the first embodiment.

As shown in FIGS. 1 through 7, in one embodiment, the sleeve portion 21 is a generally annular sleeve that includes an inner surface 19 having a diameter that is sized to fit over the outside of the sidewall 111 of the earbud 100. In one embodiment, the inner surface 19 is sized to press fit over the outside diameter of the earbud 100 for a secure fit. As shown in FIG. 4, in one embodiment, the sleeve portion 21 includes a first end 30 and a second end 32 opposite the first end 30. The sleeve portion 21 may converge from the first end 30 to the second end 32 to allow the sleeve portion 21 to fit firmly over, and partially around, the sidewall 111 of the earbud 100. As illustrated, the inner surface 19 at the first end 30 of the sleeve portion has a diameter of about 13.85 mm, and the inner surface 19 at the second end 32 has a diameter of about 11.50 mm. In addition, the sleeve portion 21 of the illustrated embodiment includes a bulbous edge 34 at the second end 32 to further enhance the tight fit of the sleeve portion 21 on the earbud 100. The bulbous edge 34 reduces the stretch in the second end 32 of the sleeve portion 21 to prevent the sleeve 21 from being pulled off the earbud during activity. The size, shape and configuration of the sleeve portion 21 may vary from application to application in part to accommodate the desired earbuds. In one embodiment, the sleeve portion 21 may be formed with dimensions smaller than those of the earphone 100 so that the sleeve portion 21 is stretched onto the earphone 100, which results in the sleeve portion 21 gripping the earphone 100.

Figure 2:
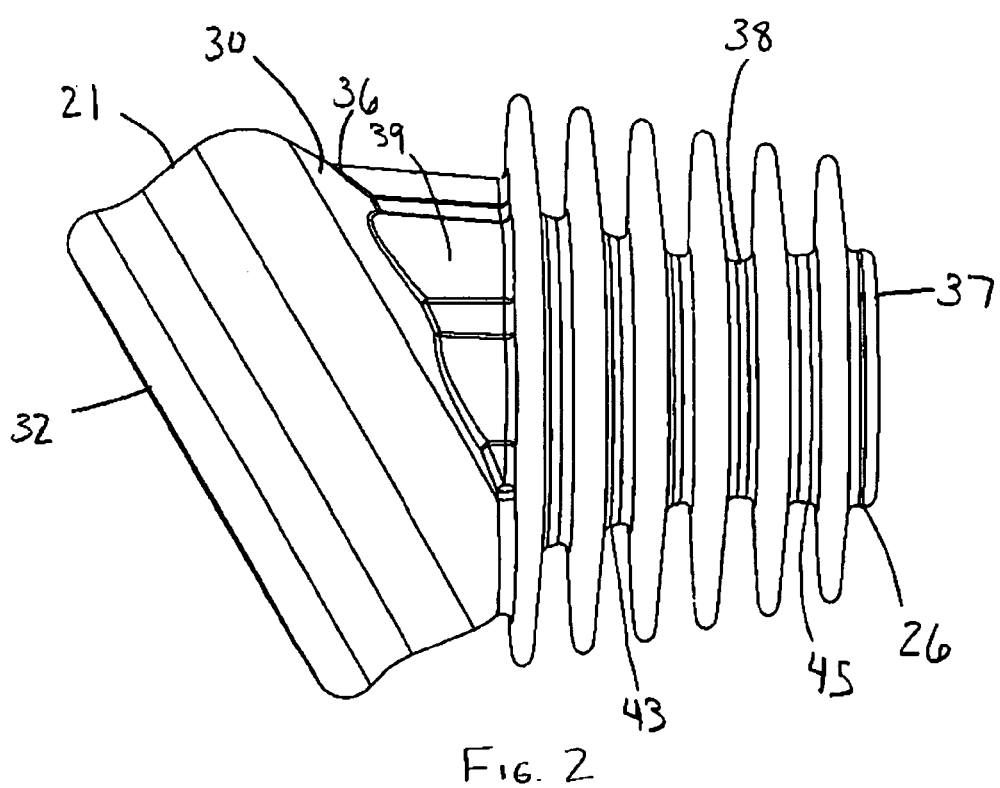
FIG. 2 is a side view of the in-ear adapter according to the first embodiment of the invention.
Figure 3:
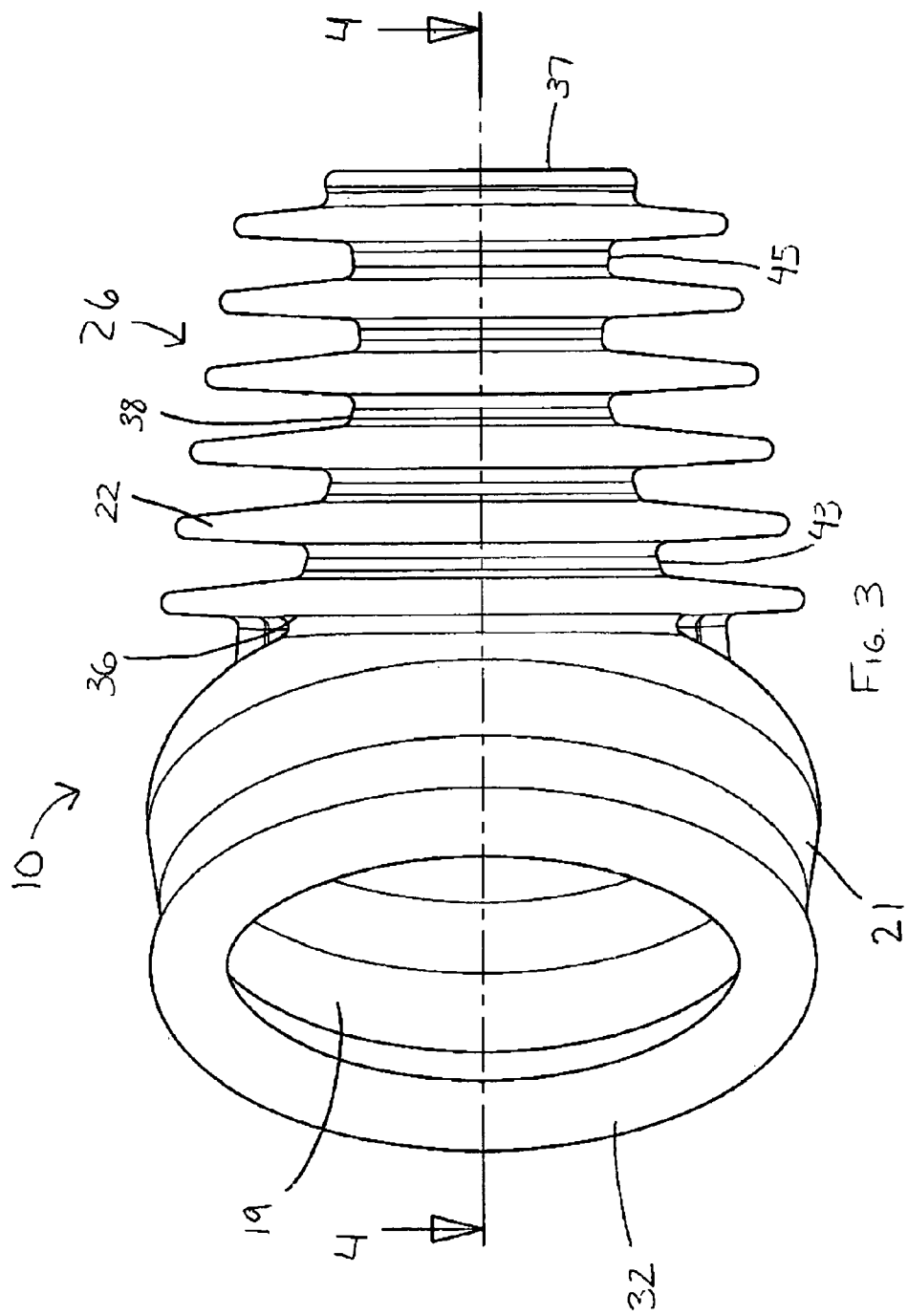
FIG. 3 is bottom view of the in-ear adapter according to the first embodiment of the invention.
Figure 25:
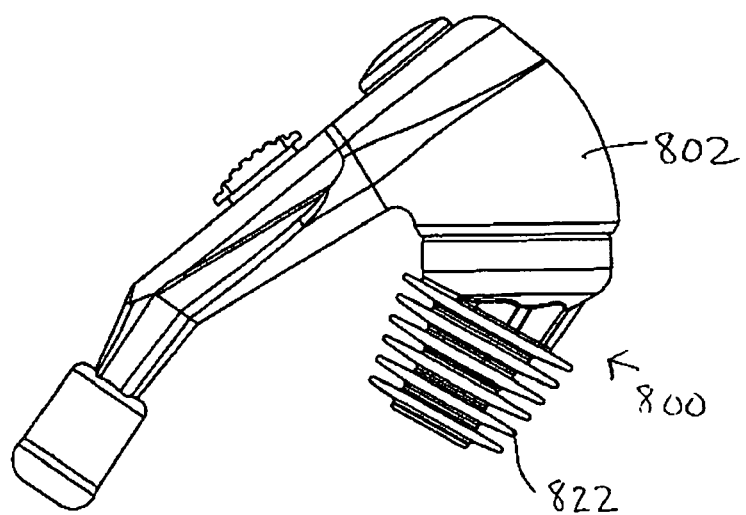
FIG. 25 is a side view of the in-ear adapter of FIG. 24.
Figure 26:
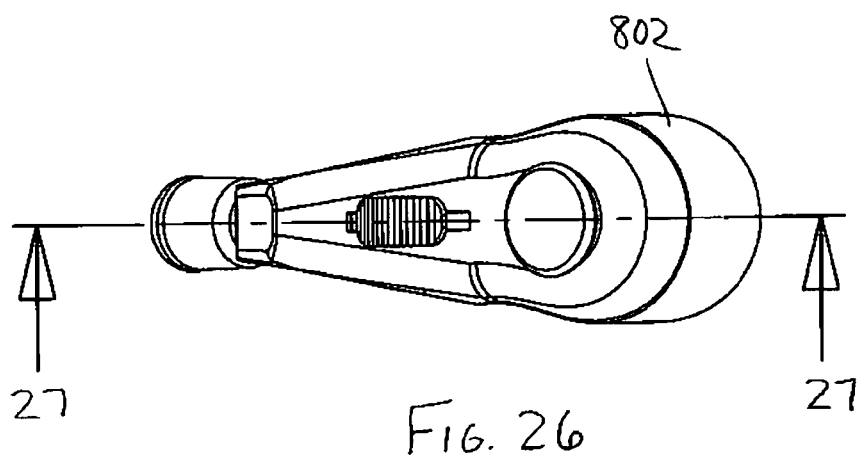
FIG. 26 is a top view of the in-ear adapter of FIG. 25.
Figure 27:
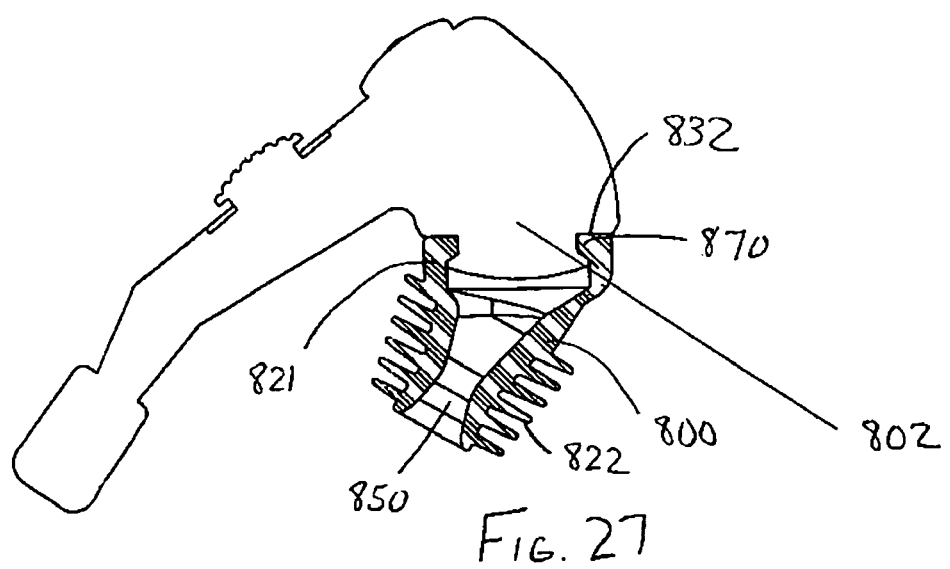
FIG. 27 is a cross-sectional view of the in-ear adapter of FIG. 25 taken along line 27-27 in FIG. 26.
Figure 30:
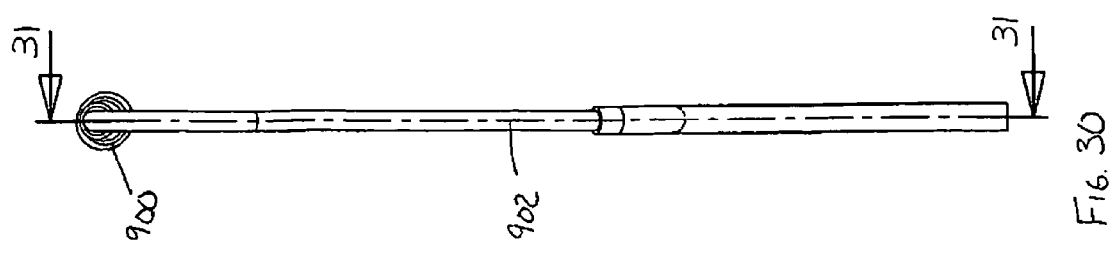
FIG. 30 is a side view of the in-ear adapter of FIG. 28.
Figure 29:
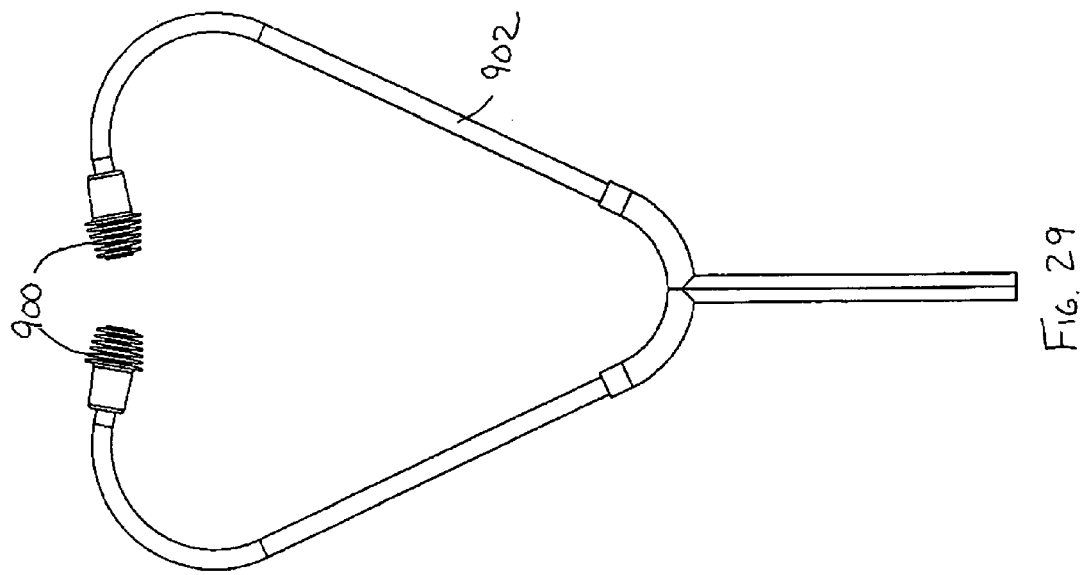
FIG. 29 is a front view of the in-ear adapter of FIG. 28.
Figure 31:
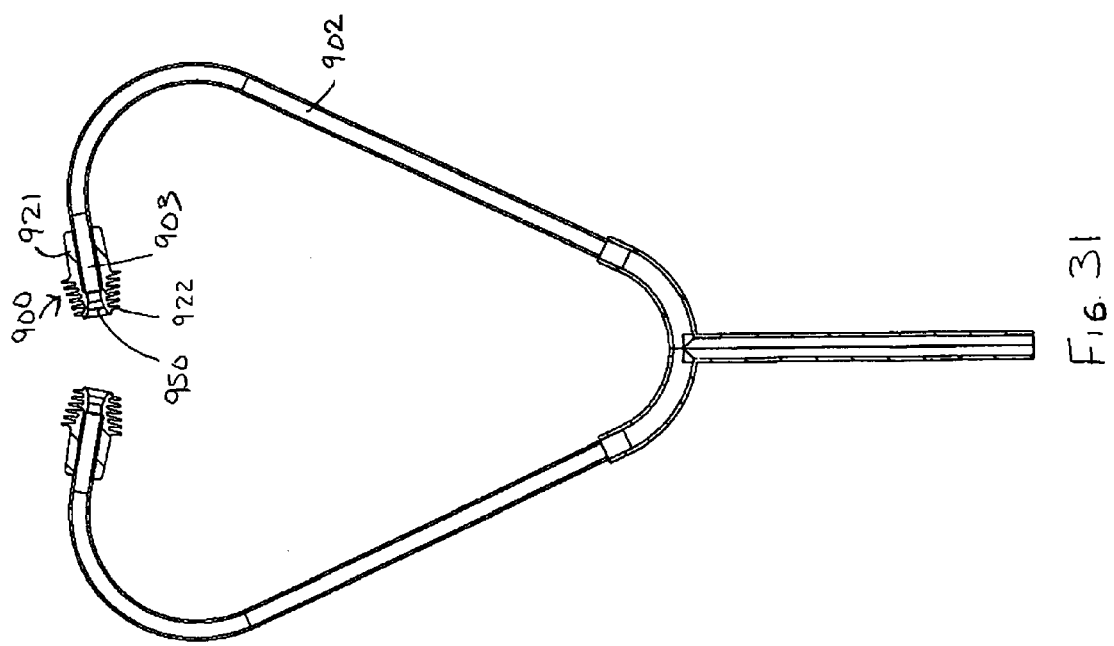
FIG. 31 is a sectional view of the in-ear adapter of FIG. 28 taken along line 31-31 in FIG. 30.
Figure 32:
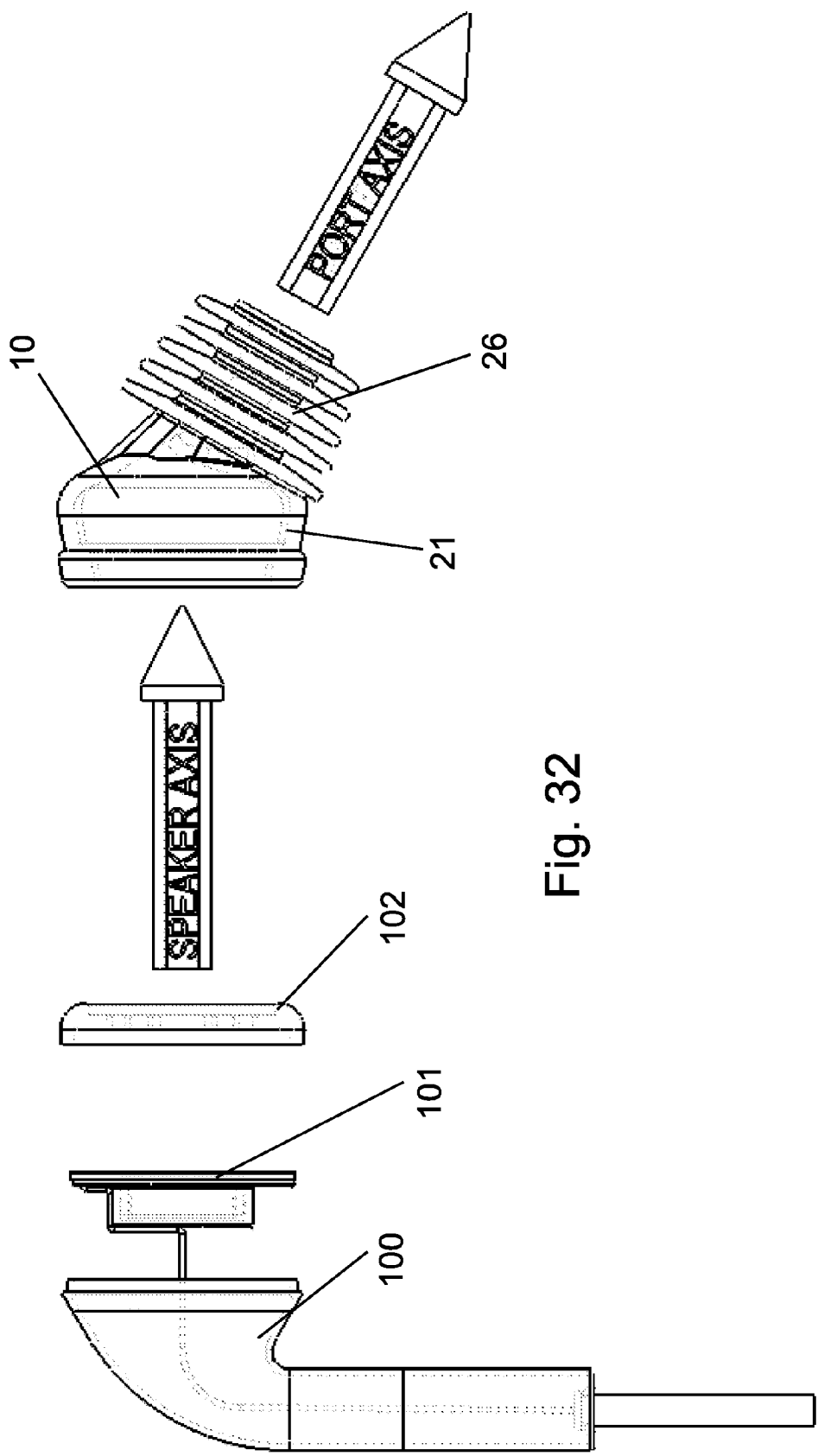
FIG. 32 is an exploded view of an earphone and an in-ear adapter with annotations indicating a speaker axis and a port axis.

Extending away from the sleeve portion 21 is an ear portion 26, which in the illustrated embodiment is a tubular projection having a first end 36 attached to the first end 30 of the sleeve portion 21 and a second end 37 opposite the first end. The ear portion 26 has an outer surface 38 and an inner surface 40 opposite the outer surface 38. The inner surface 40 defines an opening or channel 50 for transmission of sound from the speaker through the adapter 10. The ear portion 26 may be formed integrally with the sleeve portion 21, for instance, by injection molding. The ear portion 26 defines a length between the first and second ends 36, 37, which may vary from application to application and is typically between about 9 mm to 13.5 mm. In one embodiment, the length of the ear portion 26 extends along an axis that is angled from the axis of the sleeve portion 21. As illustrated, the ear portion 26 is angled about 30 degrees from the sleeve portion 21, although the adapter 10 may be constructed with no angle between the sleeve portion 21 and the ear portion 26, or another desired angle. As shown, the angle is created by an extension panel in the ear portion 26, spacing the ear portion 26 from a segment of the sleeve portion 21. In one embodiment, the angle of the ear portion with respect to the sleeve helps to redirect the sound exiting the speaker into the ear while also allowing the earbud, including any portion of the earbud such as the stem and wire or body of a Bluetooth earpiece as shown in FIG. 25 to be positioned as preferred by the user. The speaker axis is typically angled within the ear when nested. Speakers generally have an electromagnetically driven diaphragm that strokes back and forth in a single linear direction to produce sound. This linear motion defines an axis in the linear direction and is the direction of the emitted sound wave. This direction is referred to herein as the 'speaker axis'. The axis of the sound port is perpendicular the face of the speaker and in the center of the final exiting sound port. FIG. 32 provides a depiction of an earbud 100 including a speaker 101, speaker port 102 and sleeve portion 21 of an adapter 10 aligned along a speaker axis and the ear portion 26 aligned with respect to the speaker axis and defining a port axis. The ear portion 26 is formed with a thickness between the inner 40 and outer 38 surfaces that permits the ear portion to flex and deform when inserted into the ear canal. In one embodiment, the thickness of the ear portion 26 is between about 1 mm to 3 mm. In the embodiment shown in FIGS. 1-7, the outer surface 38 of the ear portion 26 is shaped to generally follow the twin cone shape of the inner surface 40, which is described in more detail below. As shown in FIG. 2, a first portion 43 of the outer surface 38 has a converging cone shape and a second portion 45 of the outer surface 38 has a diverging cone shape. As discussed further below in connection with the alternative embodiments, the shape of the outer surface 38 may vary from application to application.

In one embodiment, a plurality of fins 22 extend from the outer surface 38. The fins 22 may be formed integrally with the same material as the ear portion 26, such that they can flex to readily conform to the ear canal. In one embodiment, the fins 22 are approximately evenly spaced apart along the length of the tubular projection 26, between the first and second ends 36, 37, for example, at about 1.75 mm apart. Alternatively, the spacing may vary, including variations in spacing between individual fins 22 along the length of the ear portion 26. In the illustrated embodiment, each fin 22 extends continuously around the circumference of the outer surface 38 of the ear portion 26, although, alternatively, the fins 22 may be intermittent segments, with each segment being spaced from another segment around the circumference of the ear portion 26, and along the length of the ear portion 26. As illustrated, the fins 22 have dimensions that enable them to flex easily for comfort while still providing the desired retention and sound isolation when they are inserted into the ear canal. More flexible fins 22 may provide a more comfortable feel and may facilitate removal of the adapter 10 from the ear canal. Each fin 22 includes a base 42 joined to the outer surface 38 of the ear portion 26, and a tip 44 opposite the base 42. In one embodiment, the fins all have approximately the same height h, from base 42 to tip 44 which is between about 2.75 mm and 3.5 mm tall, although the fin heights may vary from fin to fin. The fins 22 may each have a nearly uniform thickness t, however, in the illustrated embodiment, the thickness tapers from about 0.5 mm at the tip 44 to about 0.75 mm to 1 mm at the base 42. The average thickness of the fins is between about 0.4 and 1.0 mm. Typically, the fin height is at least two times the average fin thickness and the fin thickness is not greater than 1.5 mm at the base, but this is not necessary and the height to thickness ratio may vary from application to application. If desired, different fins 22 may follow different thickness profiles. The fins 22 illustrated in FIGS. 1-7 are shown with optional radii at the tip 44 and base 42. Although shown as having a full radius tip 44, the shape of the tips 44 of the fins 22 may vary from application to application, as desired.

In one embodiment, the fins 22 are generally linear between the base 42 and tip 44. In the embodiment of FIGS. 1-7, they extend outwardly from the outer surface 38 of the ear portion 26 at a slight angle of about 6 degrees towards the sleeve portion 21, however, they may be perpendicular to the outer surface 38, or may extend at a different angle. In the illustrated embodiment, the height h of each fin 22 is approximately at least one-half the size of the diameter of the outer surface 38 of the ear portion 26 to provide a desired amount of flexibility to the fins 22 while maintaining the desired retention and sound isolation qualities. Of course, the spacing, height and thickness of the fins 22 may vary from application to application. As perhaps best shown in FIG. 6, the fins 22 may be oval in shape when viewed from the front to more closely match the shape entry to the ear canal. In the illustrated embodiment, the fins 22 are slightly oval, with a width that is approximately 90% of the height. These proportions may vary from application to application as desired. For example, in some applications, the fins 22 may be essentially circular. Finally, the illustrated embodiment shows a design with six fins 22 spaced apart along the length of the ear portion 26, with the first fin 22 spaced slightly from the second end 37 of the ear portion 26, however, other numbers of fins 22 may be used.

As further shown in FIG. 4, the interior surface 40 of the ear portion 26 may have a shape that is designed to tune the adapter 10 for improved acoustics. As shown in FIG. 4, in one embodiment, the inner surface 38 of the tubular projection defines a twin cone air channel 50. The air channel 50 generally includes a lead-in portion 51, a converging cone 52, a transition portion 54 and a diverging cone 56. The lead-in portion 51 provides a smooth curved transition from the speaker to the converging cone 52. In the illustrated embodiment, the converging cone 52 is shaped to provide a relatively smooth transition from the full diameter of the earphone to the reduced diameter of the transition portion 54. The converging cone 52 converges the sound wave coming from the speaker down to the transition portion 54. As illustrated, the transition portion 54 relatively smoothly joins the converging cone 52 to the diverging cone 56. The diverging cone 56 functions to diverge and amplify the sound wave from the reduced diameter of the transition portion 54 into the ear canal. The diverging cone 56, with flared end 57 provides a relatively smooth transition from the transition portion 54 to the point where the sound exits the adapter 10 and passes into the air cavity in the ear canal. Although the cone angles and the shapes of the curved transitions may vary from application, the cone angles will typically range between 5 and 25 degrees per side. In the illustrated embodiment, the converging cone 52 has an angle of approximately 15 degrees and the diverging cone 54 has an angle of about 12 degrees. Generally speaking, it has been found that small cone angles may better reproduce lower frequencies and higher cone angles may better reproduce mid and upper range frequencies. Longer diverging cones also may yield more amplification. It may be desirable to adjust the rate at which the cones increase and decrease in angle to provide a pleasing balance of bass, mid and upper frequencies given the speaker driver being used. Using a continuous curved or elliptical profile in both the converging and diverging cones may also be desirable to achieve a desired tonality. This approach would eliminate the fixed angles shown for the converging and diverging cones but does not depart for the intent of the invention.

The illustrated twin cone air channel 50 provides improved sound quality at least in part because the smooth curves in the interior surface 40 of the ear portion reduce or eliminate abrupt changes in the cross-sectional area of the air channel 50. Abrupt changes in the cross-sectional area of the air channel may cause significant changes in both sound wave pressure and air particle velocity. These disruptions may cause undesirable acoustical distortions and reflections. The illustrated twin cone design reduces or eliminates these distortions and reflections, thereby providing improved acoustical performance—perhaps most notably with higher frequency sounds, such as cymbals and snare drums, which are given more clarity and presence. To assist in understanding the advantages of the twin cone design shown in FIG. 4, it may be helpful to view the entire sound pathway between the earphone speaker and the ear drum as a single tubular passageway. Speakers come in many sizes. To have good sounding bass frequencies, it is desirable to use a speaker with sufficient surface area to push a significant volume of air. Speaker drivers in the 10 mm to 15 mm range may be better at producing bass than smaller drivers. Regardless of the speaker size selected, the converging cone 52 functions in part to gradually converge and reduce the sound waves in area from the speaker diameter as the sound travels through the tubular projection 26 down the ear canal. At the end of the converging cone 52 is the transition portion 54, which provides a gradual transition into the diverging cone 56. The diverging cone 56 gradually increases in area to smooth out the transition as the sound wave enters the air cavity inside the ear canal on its way to the ear drum. The diverging cone 56 does this while also providing a slight amplification of the sound wave. With the twin cone system, area changes are more gradual along the entire pathway from the speaker to the ear drum while more directly aiming the sound down the ear canal. Generally speaking, the objective with the illustrated twin cone air channel is to gradually taper the area of the channel to a point or region then gradually increase the area. Although the illustrated cones have essentially straight walls that taper at a generally constant angle, the cones could have essentially any number of funnel like or curved shapes.

Although the illustrated air channel 50 provides improved sound quality with typical earphones, the size, shape and configuration of the air channel 50 may vary from application to application. In an alternative embodiment, shown FIG. 16, the inner surface 140 of the air channel 50' tapers as it extends away from the sleeve portion 121, forming a generally frustoconical shaped cavity within the tubular projection 126. Similar to the twin cone design, the cone shaped cavity funnels the sound from the earphone toward the ear canal, similar to the function of the conventional ear trumpet, and amplifies the sound that is actually heard by the wearer. The exact shape of the cone may be varied to tune the adapter for improved acoustics. In one embodiment, such as that shown in FIGS. 13 and 22, the air channel 50" may flare outwardly or may be angled near the port opening at the end of the tubular projection 26 opposite the sleeve portion 21 in order to provide some of the effects of the diverging cone discussed above.

III. Alternative Embodiments

Figure 8:
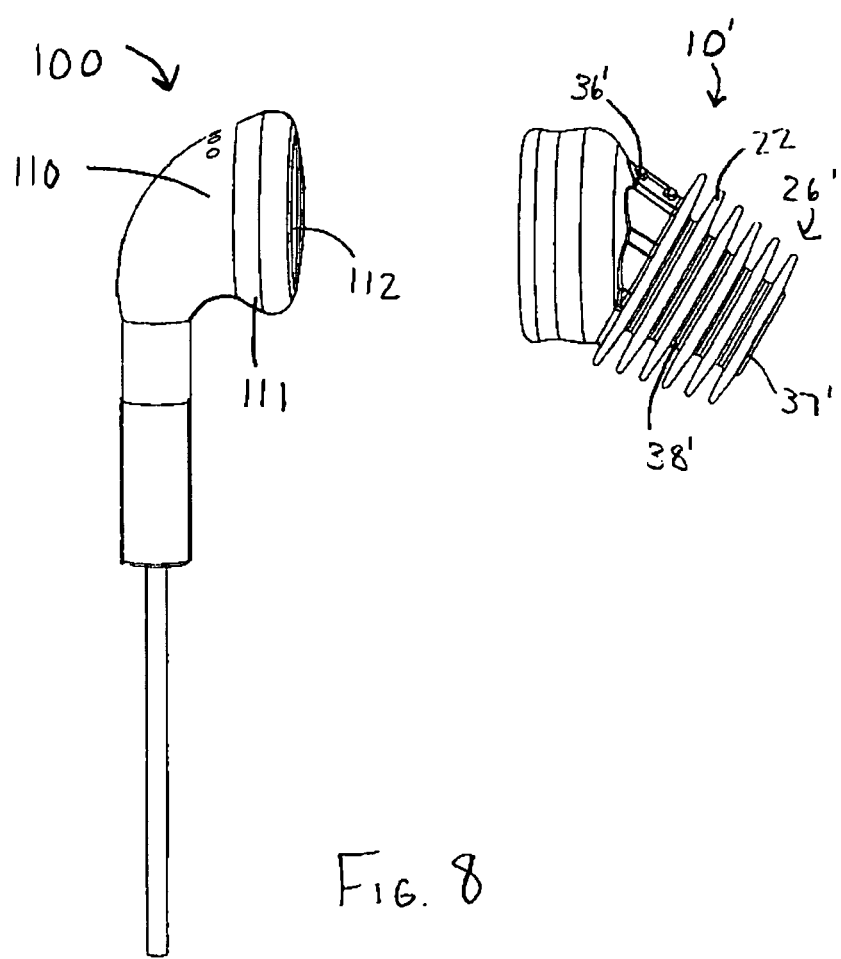
FIG. 8 is a side exploded view of an earbud and the in-ear adapter according to an alternative embodiment of the invention.
Figure 9:
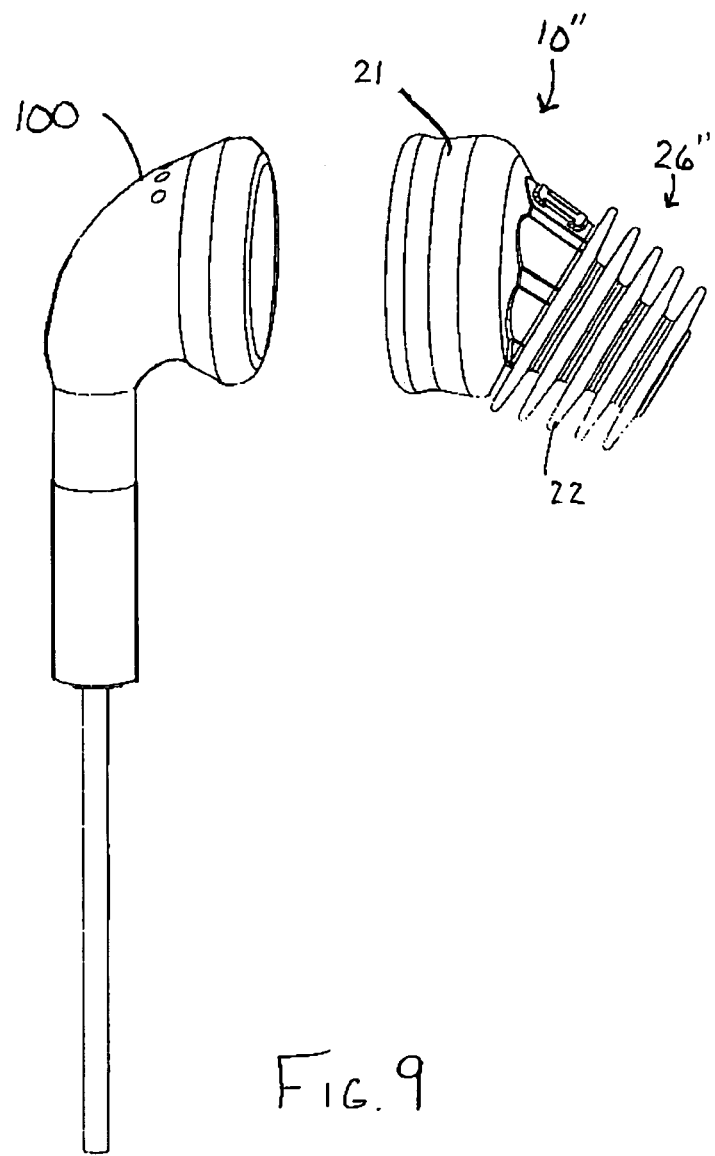
FIG. 9 is a side exploded view of an earbud and the in-ear adapter according to another alternative embodiment of the invention.
Figure 10:
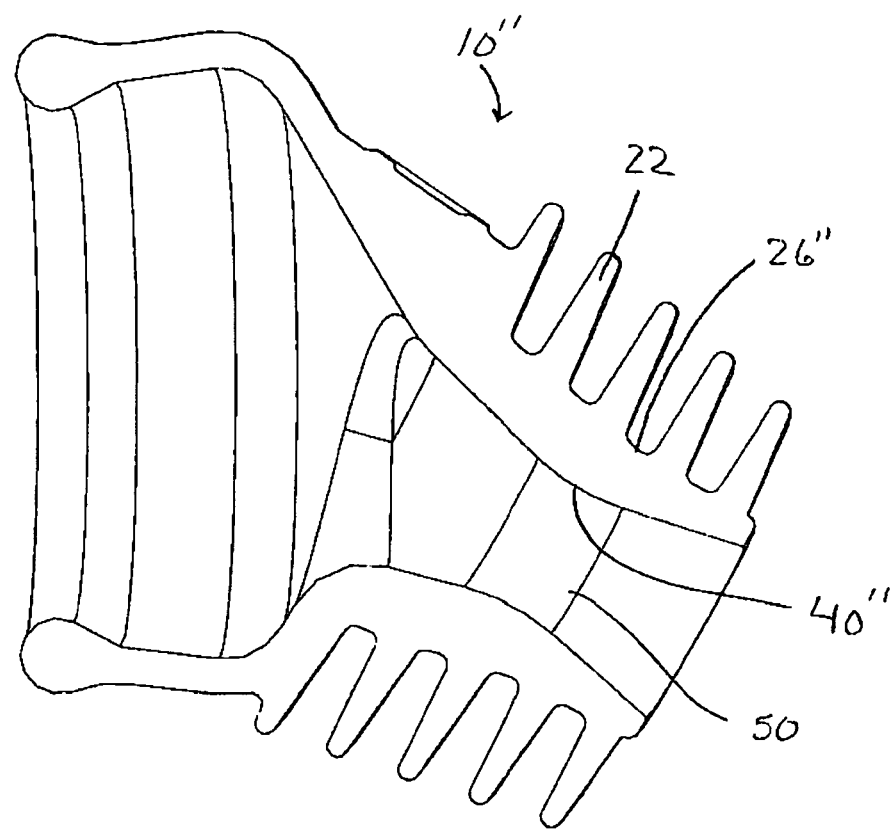
FIG. 10 is a side cross sectional view of the in-ear adapter of FIG. 9.

FIGS. 8-31 show various variations and alternative embodiments of the adapter 10 described above. The adapter 10' shown in FIG. 8 is substantially similar to the adapter 10 shown in FIGS. 1-7, except that the outer surface 38' of the ear portion 26' is cone shaped, such that the outer surface 38' continuously converges from the first end 36' to the second end 37'. The adapter 10" shown in FIG. 9 is substantially similar to the adapter of FIG. 8, except that the length of the ear portion 26" of adapter 10" is shorter, and the ear portion 26" includes only five fins 22 instead of six. Additional variations of the length of the ear portion and the number of fins are possible, depending on the desired retention characteristics, or for the manufacture of adapters of different sizes to accommodate different size ears. FIG. 10 shows a cross section of the five fin adapter, wherein the inner surface 40" includes a twin cone air channel 50.

Figure 11:
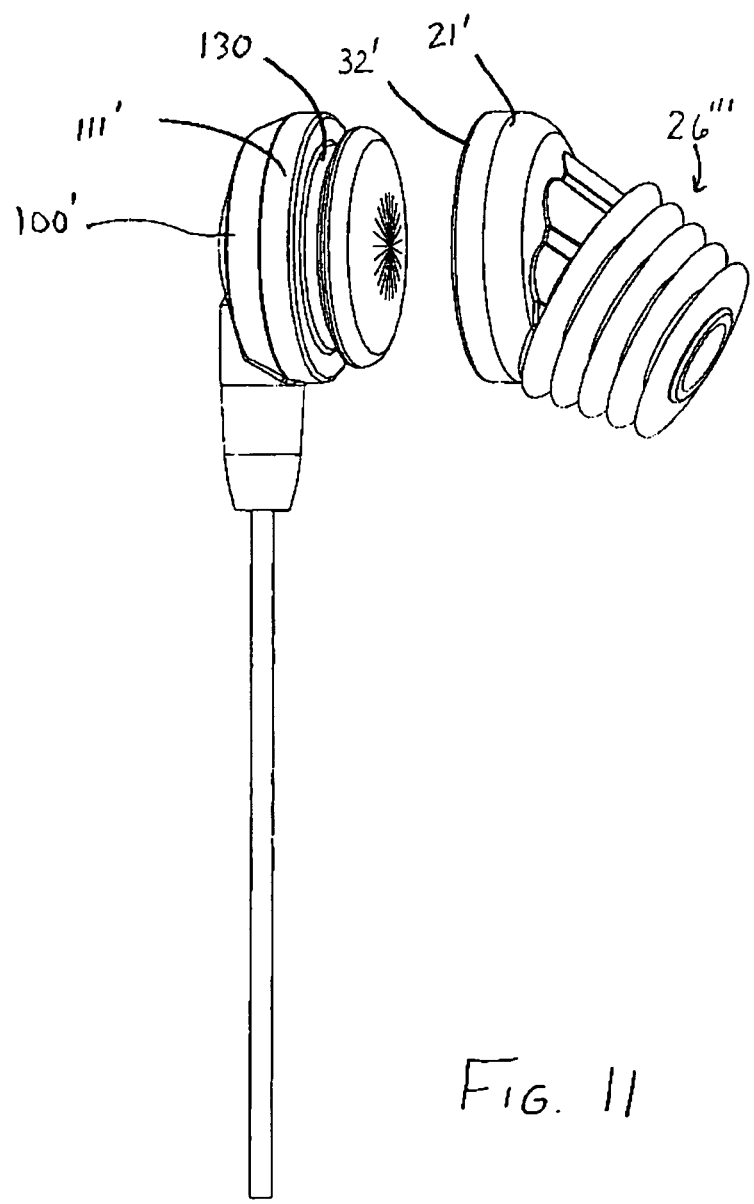
FIG. 11 is an exploded perspective view of an earbud and the in-ear adapter according to another alternative embodiment of the invention.
Figure 12:
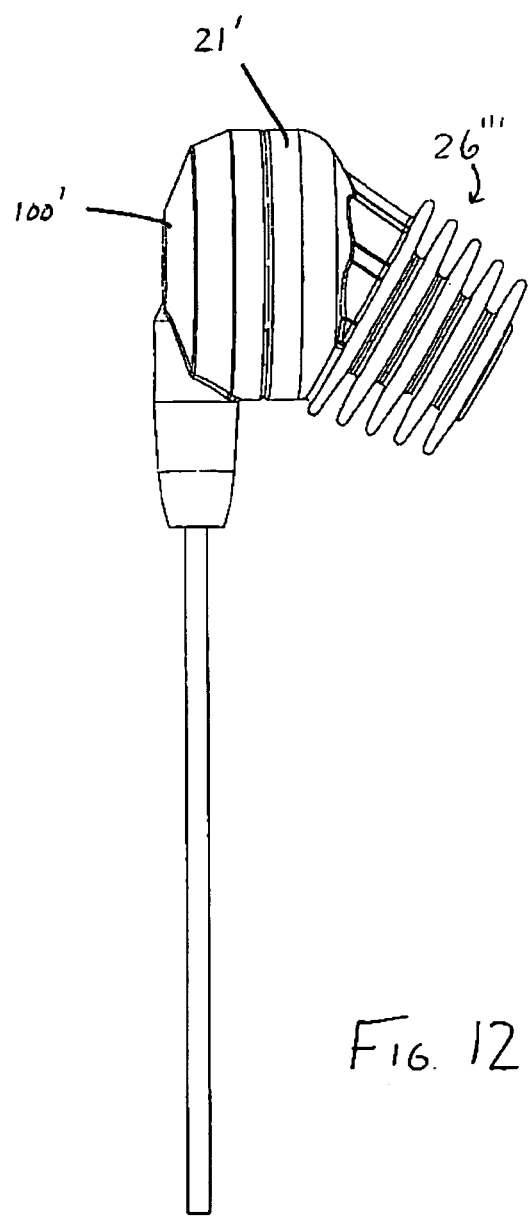
FIG. 12 is a side view of the in-ear adapter of FIG. 11 mounted to the earbud.
Figure 13:
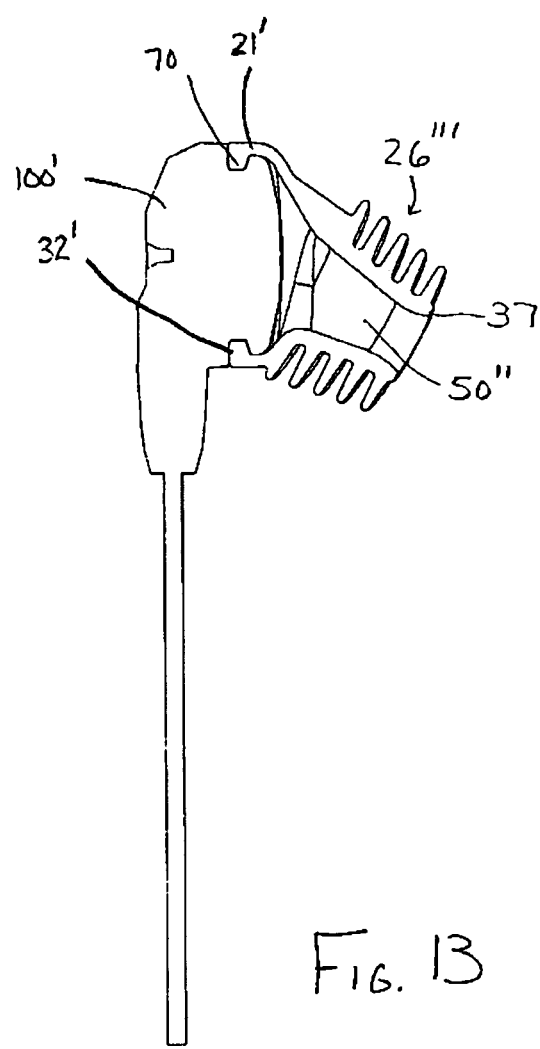
FIG. 13 is a cross sectional view of FIG. 12.

FIGS. 11-13 illustrate an alternative sleeve portion 21' that is formed with an undercut 70 at the second end 32' of the sleeve 21'. In the FIG. 10-13 embodiment, the undercut 70 is sized and shaped to fit within an annular groove 130 that is formed in the sidewall 111' of the earbud 100'. As noted above, the air channel 50" of this embodiment is generally frustoconical, with an outward flare at the second end 37 of the ear portion 26".

Figure 14:
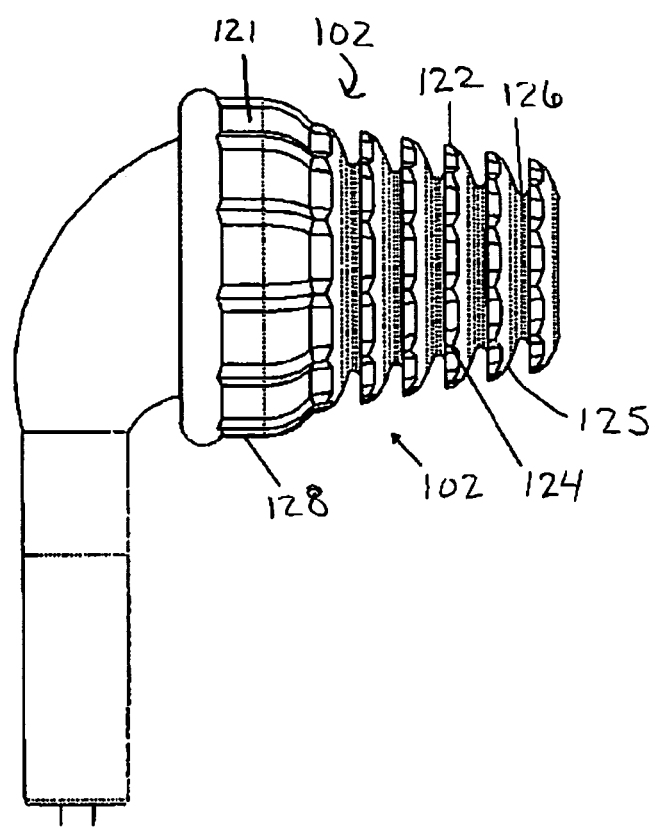
FIG. 14 is a side view of an in-ear adapter according to another embodiment of the invention shown mounted to an earbud.
Figure 15:
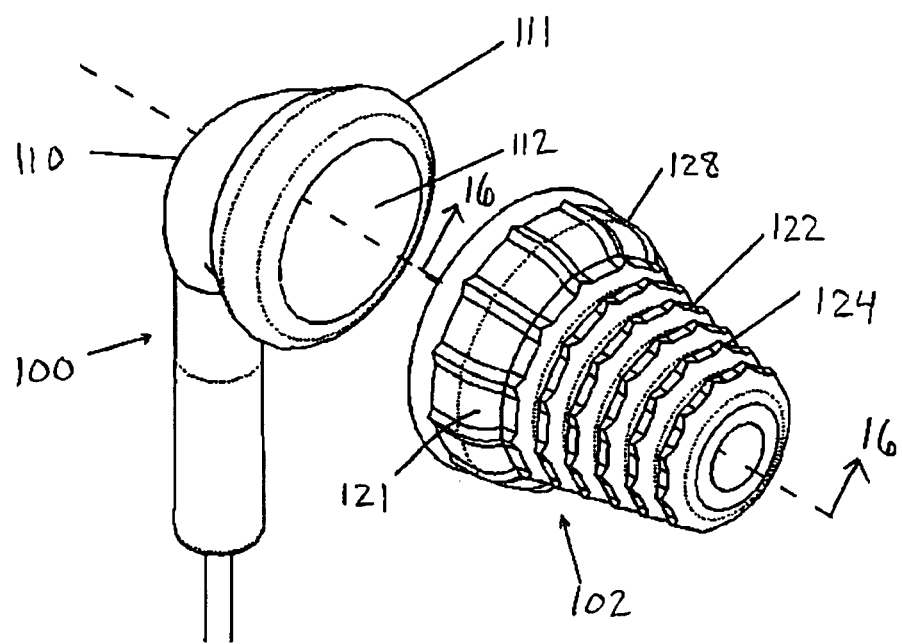
FIG. 15 is an exploded perspective view of the earbud and adapter of FIG. 14.
Figure 16:
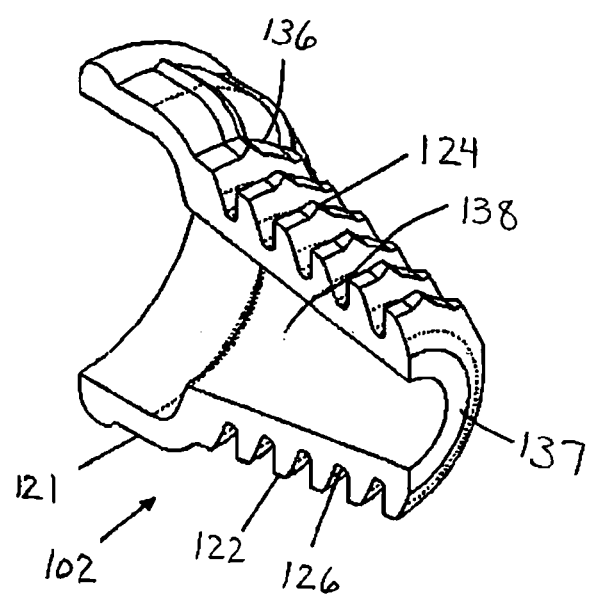
FIG. 16 is a cross sectional view of the adapter taken along line 16-16 in FIG. 15.

FIGS. 14-16 show another alternative embodiment of the adapter 102 including a plurality of fins 122, each having a plurality of protrusions 124 spaced apart around the circumference of the ear portion 126. In addition, a plurality of protrusions 128 are spaced apart about the sleeve portion 121. The protrusions may be provided to increase the surface area of the fins 122 to increase the retention of the adapter 102 in the ear. In addition, as shown in FIG. 16 and described above, the inner surface 140 of the adapter 102 is cone shaped, such that it converges from the first end 136 to the second end 137 of the ear portion 126. Further, the fins 122 of this embodiment each include a generally rounded leading edge 125 that aids in inserting the adapter 102 into the ear.

Figure 17:
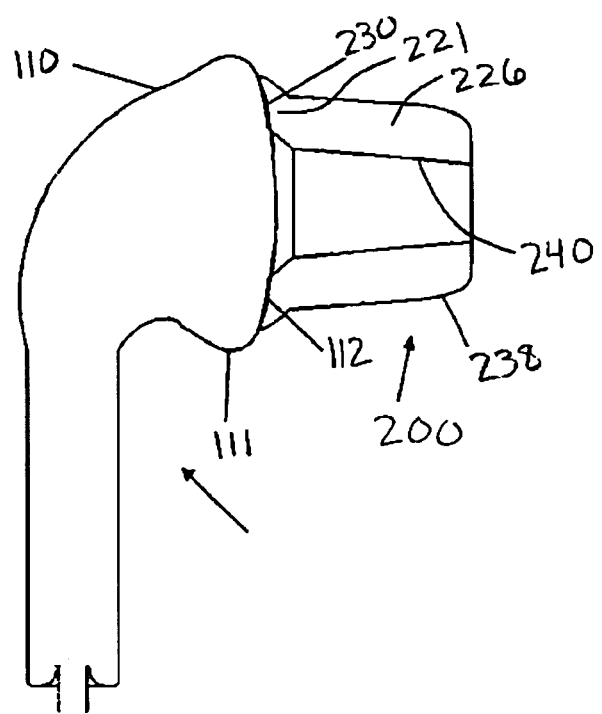
FIG. 17 is a side cross-sectional view of an in-ear adapter according to another embodiment of the present invention.

FIG. 17 shows an embodiment of the invention wherein an adapter 200 has a sleeve portion 221 that includes a face 230 that is glued to the face of the speaker 112 as an alternate means of attachment. The ear portion 226 extends away from the mounting portion as before and is thus allowed to flex both along its axis and cross section as previously described. Although not illustrated, the ear portion 226 may include fins extending from the outer surface 238, and a shaped inner surface 240, such as a twin cone shaped inner surface.

Figure 18:
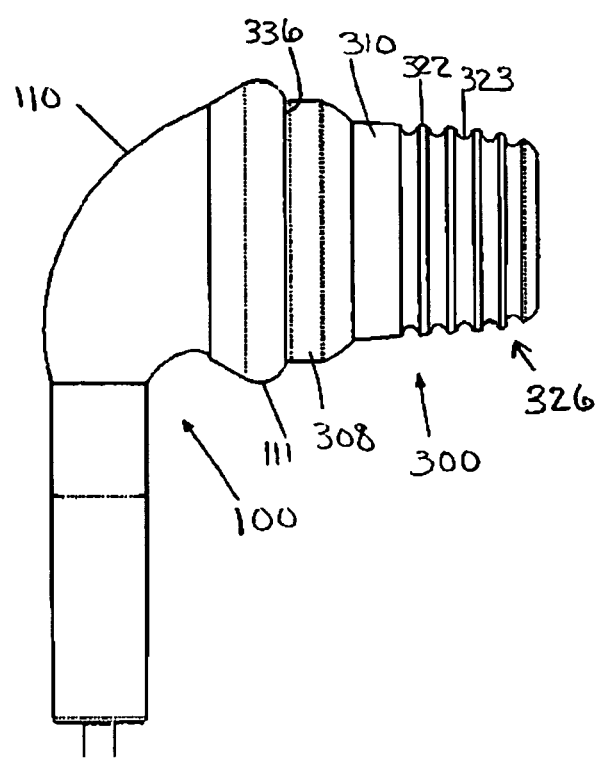
FIG. 18 is a side view of an in-ear adapter according to another embodiment of the present invention.

FIG. 18 discloses an embodiment of the adapter 300 including an ear portion 326 having a first spacer 308 extending from the first end 336 and having a generally converging cone shape, a second spacer 310 extending from the first spacer 308, and a plurality of relatively short fins 322, spaced apart by rounded valleys 323.

Figure 19:
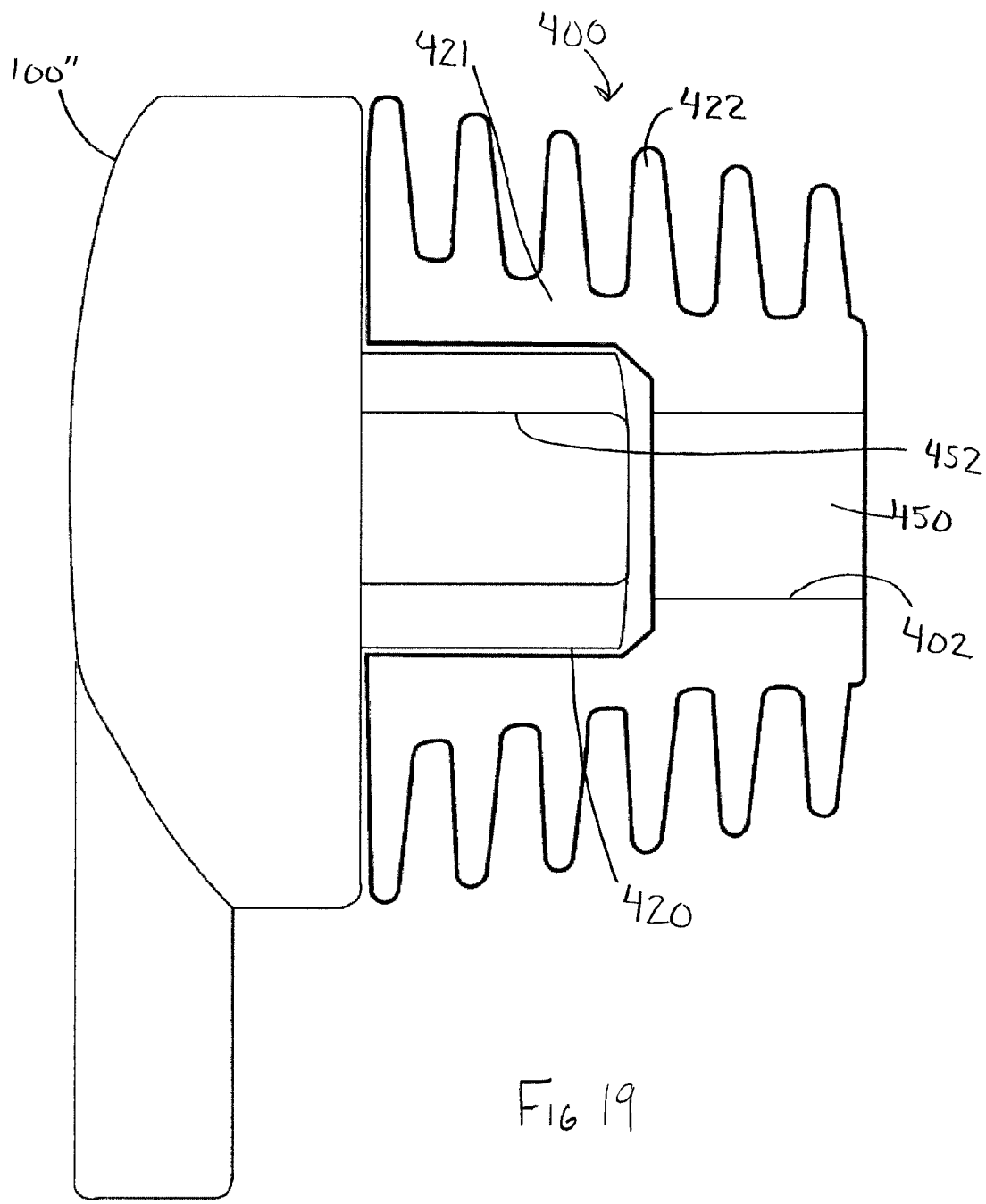
FIG. 19 is a side cross-sectional view of an in-ear adapter according to another embodiment of the present invention.
Figure 20:
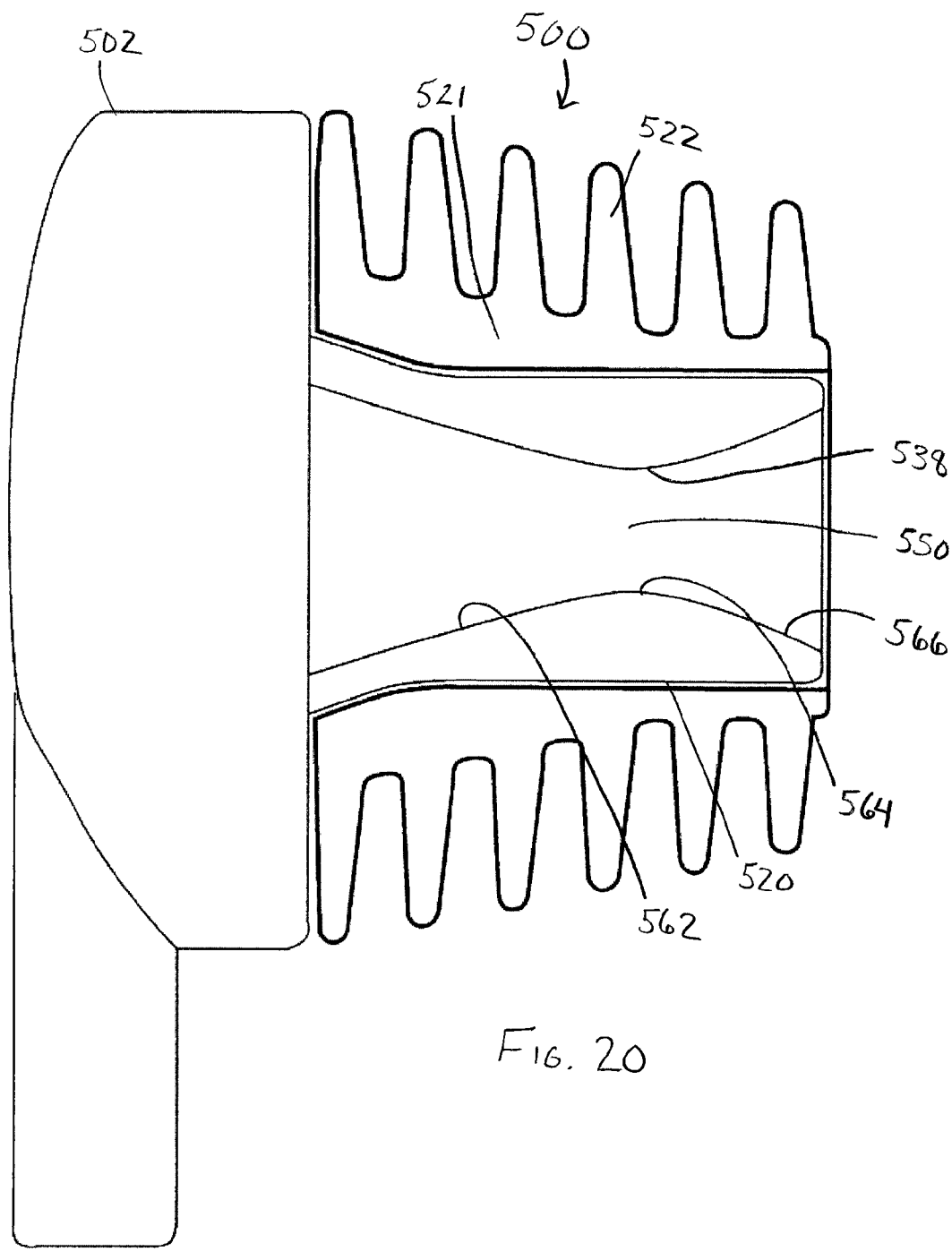
FIG. 20 is a side cross-sectional view of an in-ear adapter according to another embodiment of the present invention.
Figure 21:
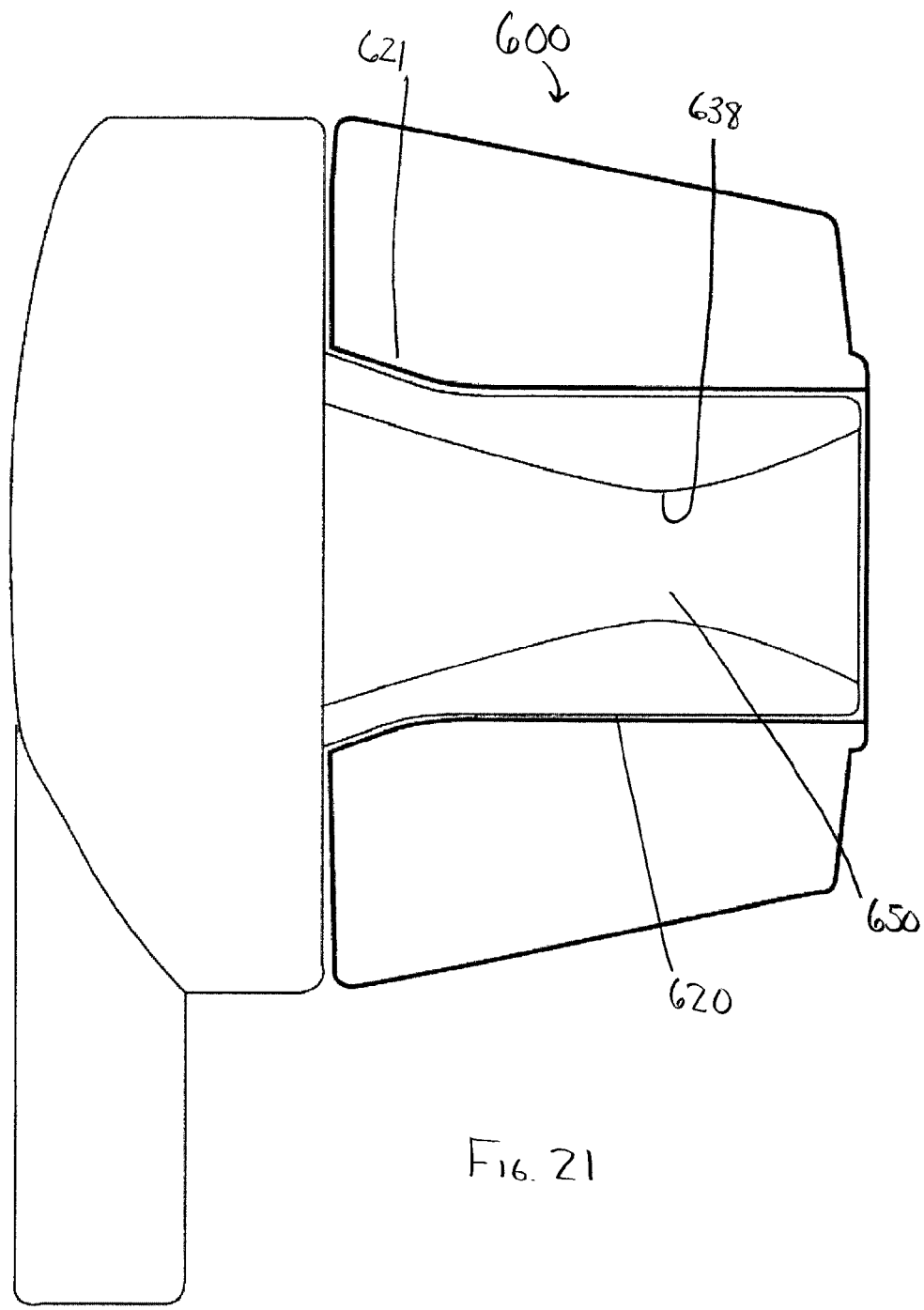
FIG. 21 is a side cross-sectional view of an in-ear adapter according to another embodiment of the present invention.

FIGS. 19-21 show alternative embodiments in which the adapter 400, 500, 600 is configured to be fitted to an earbud having a mounting post. FIG. 19 shows an adapter 400 adapted to be fitted onto an earbud 100" having a substantially straight mounting post 150. The adapter 400 generally includes a sleeve portion 421, an ear portion 426, and a plurality of fins 422 extending from both the sleeve portion 421 and the ear portion 426. The sleeve portion 421 is sized and shaped to fit snuggly over the mounting post 420. As shown, the internal diameter 452 of the mounting post 420 may coincide with the internal diameter 402 of the air channel 450. Although not shown, the air channel 450 may include a diverging cone to provide a smooth transition from the adapter 400 to the ear canal.

FIG. 20 shows an adapter 500 adapted to be fitted onto an earphone 502 having a substantially straight mounting post 520. In this embodiment, the mounting post 520 includes an inner surface 538 that defines a twin cone air channel 550. The twin cone air channel 550 generally includes a converging cone 562, a transition portion 564 and a diverging cone 566. The adapter 500 generally includes a sleeve portion 521 and a plurality of fins 522. The sleeve portion 521 is sized and shaped to fit snuggly over the mounting post 520. As shown, the mounting post 520 may define the entire air channel, thereby eliminating the need to incorporate an air channel into the adapter 500.

FIG. 21 shows an alternative embodiment of the adapter/earbud combination of FIG. 20. In this embodiment, the adapter 600 includes a sleeve portion 621 adapted to be fitted over the earphone mounting post 620, which includes an inner surface 638 defining a twin cone air channel 650. The adapter 600 of this embodiment does not include fins, but instead has a relatively smooth surface. Adapter 600 may be manufactured from soft resilient materials, such as TPU foam and viscoelastic polyurethane foam.

Figure 22:
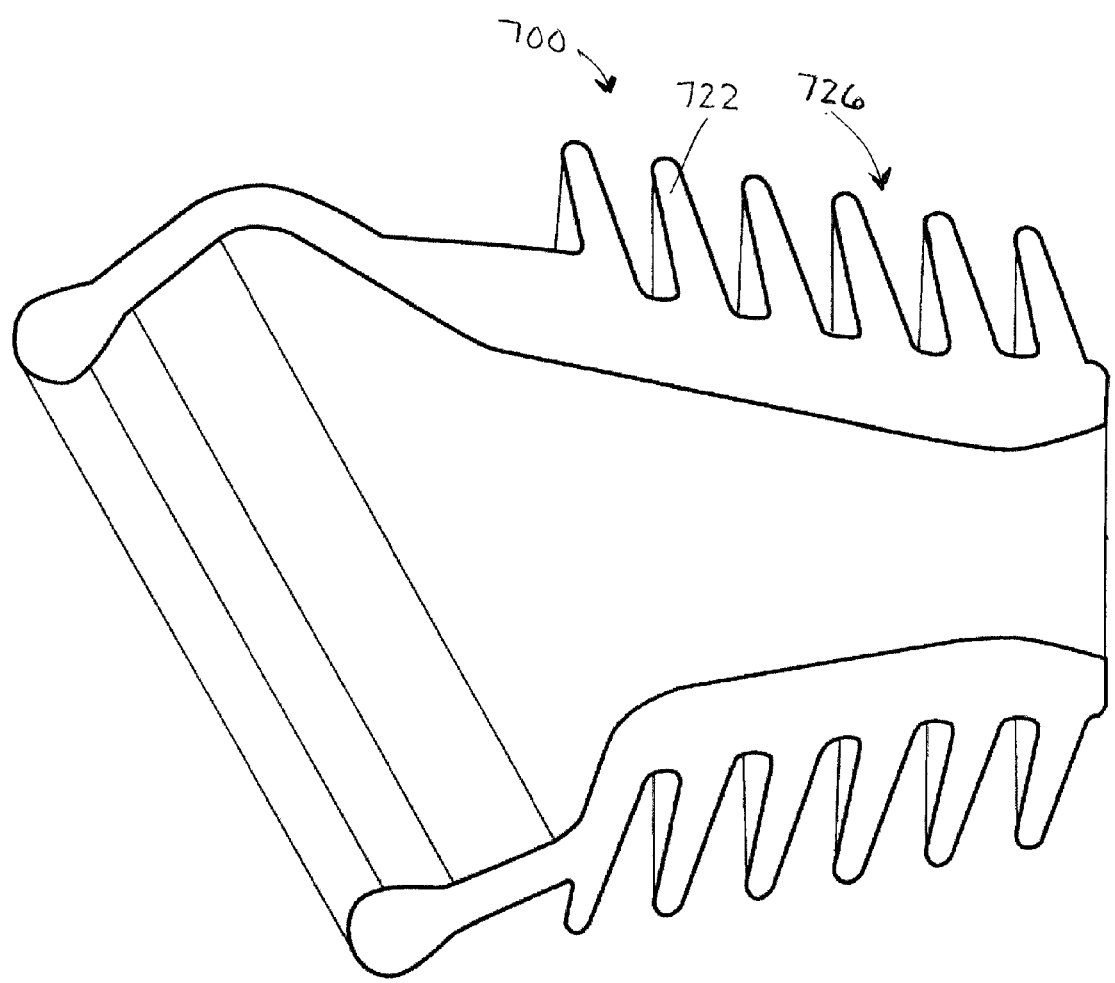
FIG. 22 is a side cross-sectional view of an in-ear adapter according to another embodiment of the present invention.
Figure 23:
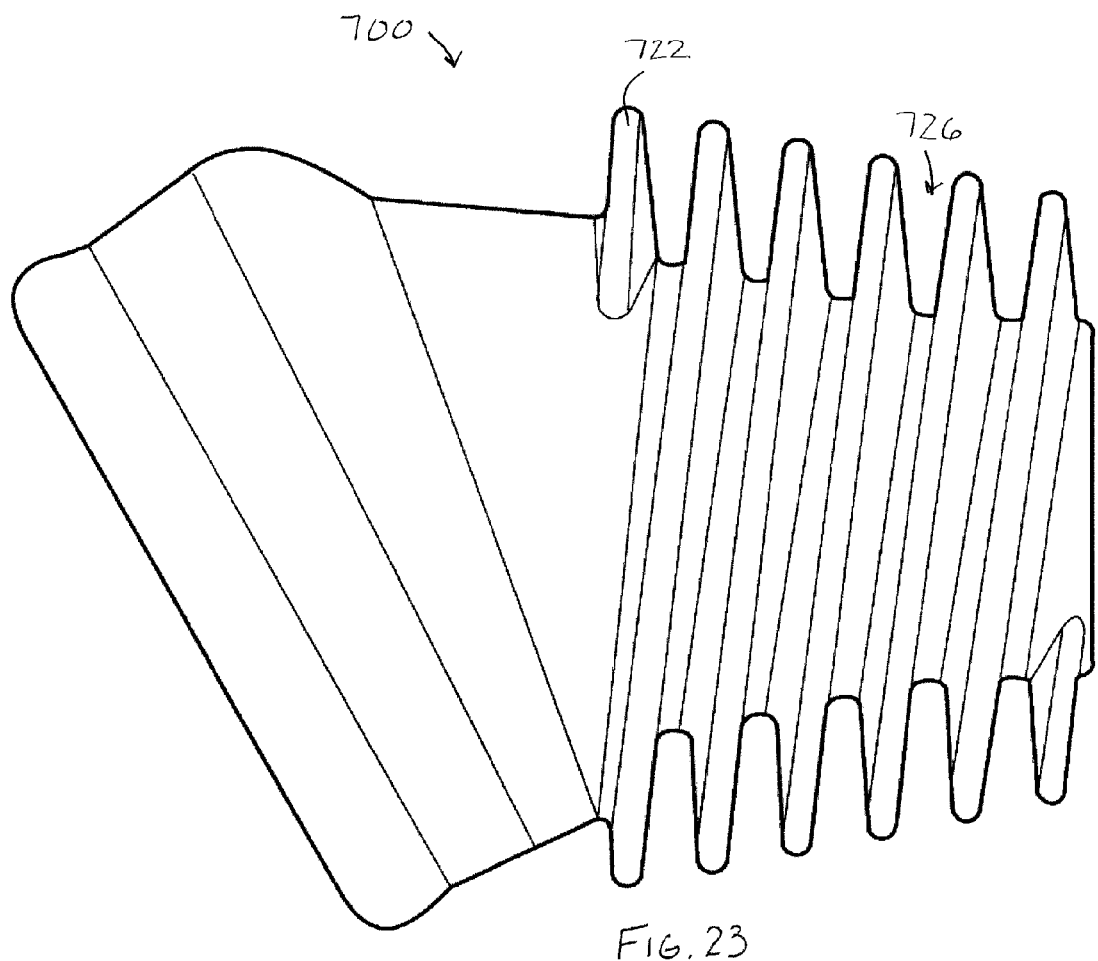
FIG. 23 is a side view of the in-ear adapter of FIG. 22.
Figure 24:
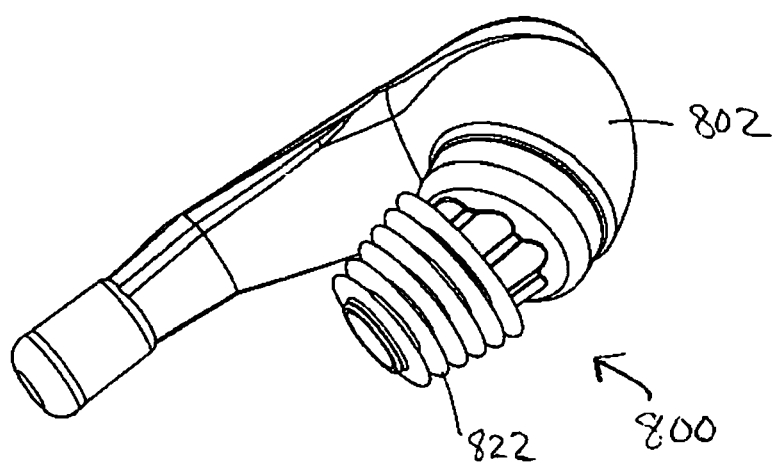
FIG. 24 is a perspective view of an in-ear adapter according to another embodiment of the present invention.

Another alternative embodiment is shown in FIGS. 22-23. FIGS. 22-23 show an adapter 700 with an alternative fin construction in which the fins are defined by a single helical rib 722 that repeatedly wraps about the ear portion 726.

FIGS. 24-27 show an embodiment of the adapter 800 attached to the earbud of a wireless or "Bluetooth" headset 802. The adapter 800 of this embodiment is substantially similar to the adapter of the first embodiment, except that the adapter 800 includes an undercut 870 at the second end 832 of the sleeve portion 821 to securely attach the adapter 800 to the Bluetooth headset 802. The adapter 802 is illustrated with six fins 822 and a twin cone air channel 850, although other variations of ribs and differently shaped air channels may be used, depending on the desired application.

FIGS. 28-31 show an embodiment of the adapter 900 attached to a stethoscope 902. The adapter 900 of this embodiment is substantially similar to the adapter of the first embodiment, except that the sleeve portion 921 is elongated and shaped to receive the generally cylindrical earbud portion 903 of the stethoscope 902 to securely attach the adapter 900 to the stethoscope 902. The earbud portion 903 of the stethoscope 902 does not include a speaker as in the previous embodiments, but, similar to the earbuds of the previous embodiments, it includes fits into a portion of the ear and includes an opening or port that emits sound. The elongated sleeve portion 921 could be a straight hole that is stretched over the cylindrical earbud portion 903. The adapter 902 is illustrated with six fins 922 and a diverging cone air channel 950, although other variations of ribs and differently shaped air channels may be used, depending on the desired application.

Figure 33:
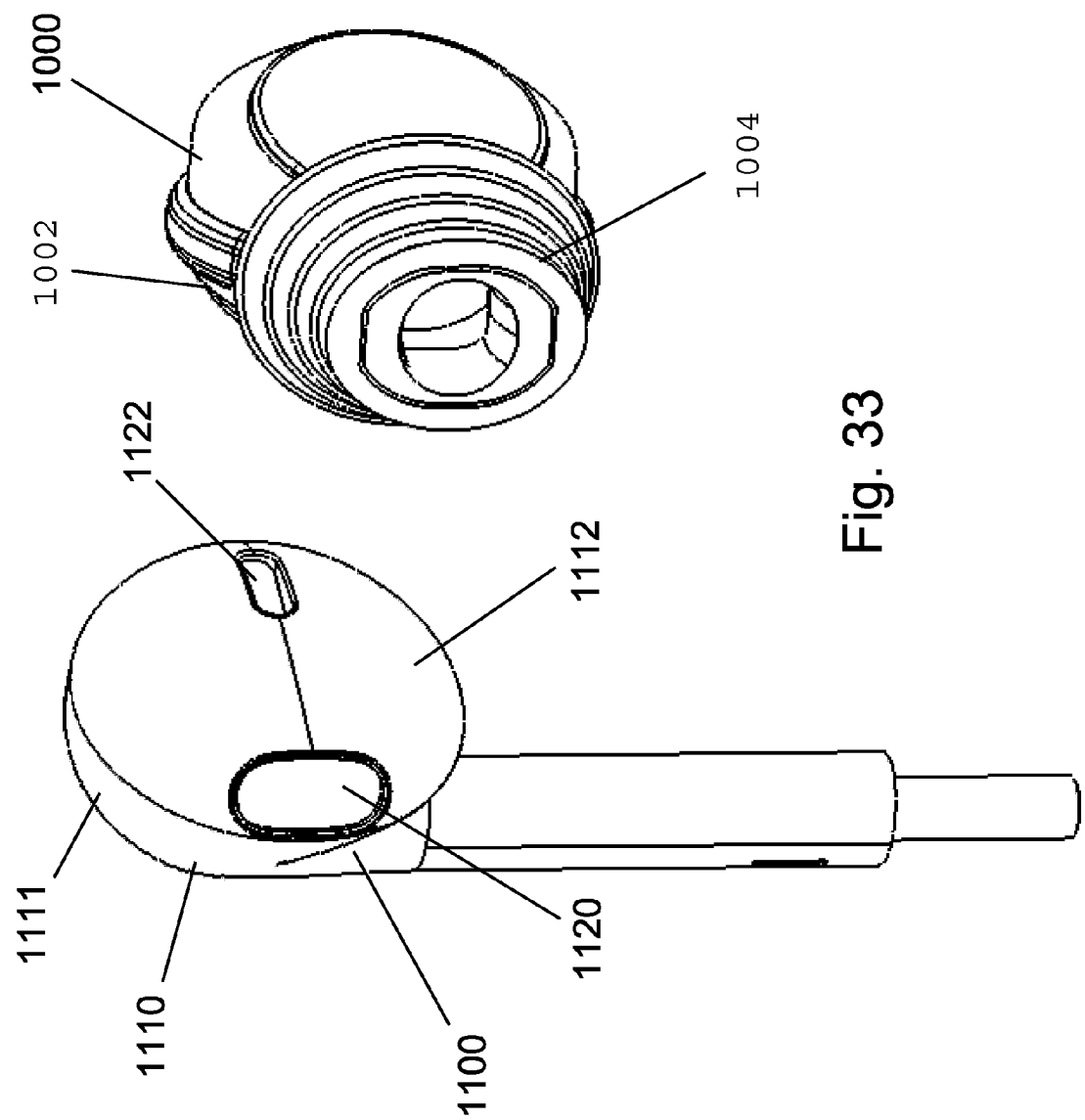
FIG. 33 is an exploded view of an earpod and an earpod style adapter according to one embodiment.
Figure 34:
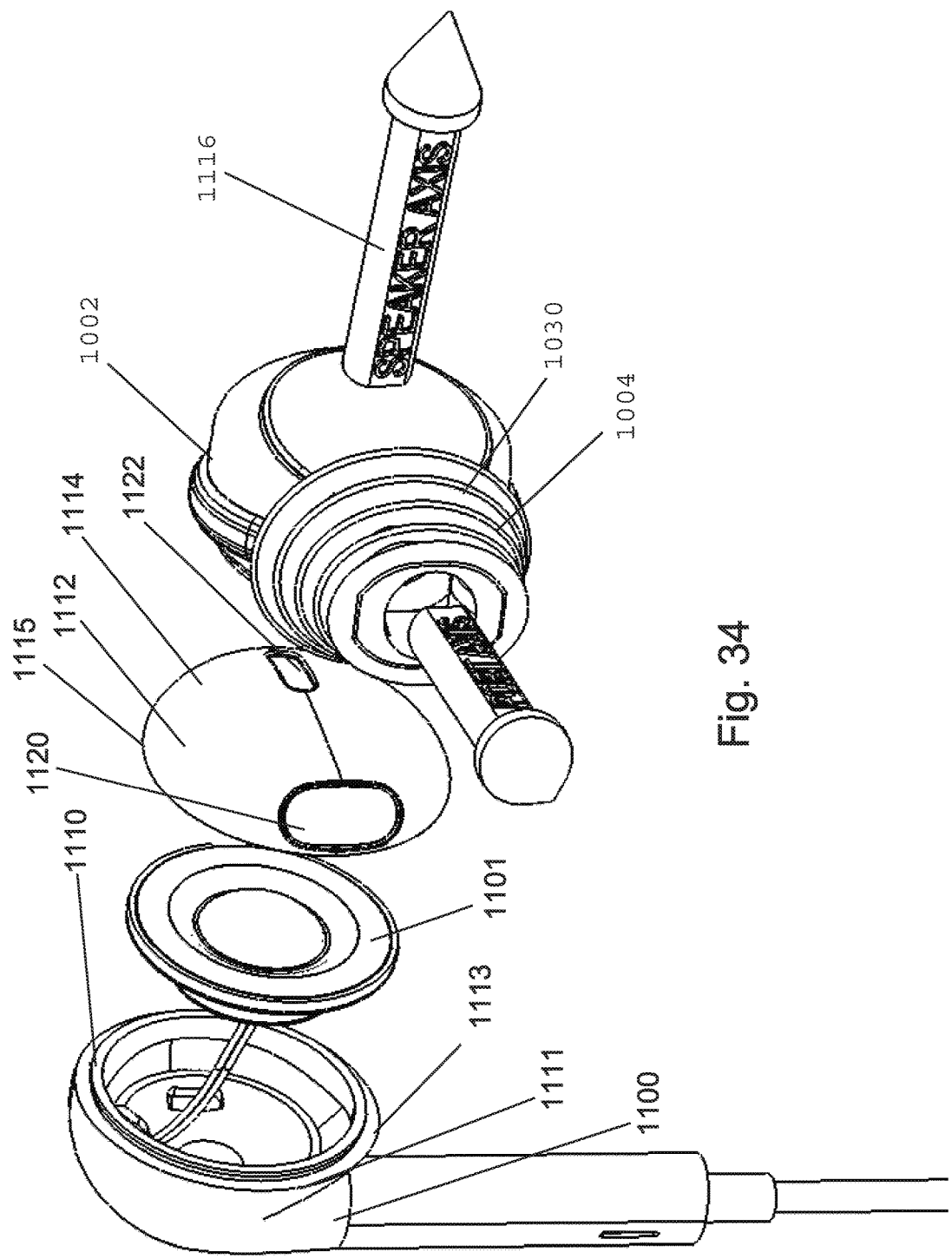
FIG. 34 is an exploded view of an earpod and the earpod style adapter.

FIGS. 33-44 show an embodiment of an adapter 1000 configured for attachment to an earpod style earphone. Referring to FIGS. 33 and 34, one example of an earpod style earphone is shown and generally designated 1100. The earpod 1100 has a speaker housing 1110 with a sidewall 1111 that terminates in a rim 1113 that is generally flush with the speaker 1101. A speaker cover 1112 is mounted to the rim 1113 of the sidewall 1111. The speaker cover 1112 is dome shaped, and includes an outer surface 1114 and a peripheral edge 1115 forming a rim adjoined to the rim 1113 of the sidewall 1111. The speaker cover 1112 may be formed of a rigid piece of plastic or other material, and may include a port or ports that direct the passage of sound. In the illustrated embodiment, the speaker cover 1112 includes an angled audio port 1120 and a straight audio port 1122. The angled audio port 1120 is positioned in the speaker cover 1112 adjacent to the peripheral edge 1115. As illustrated, the angled audio port 1120 is positioned to direct sound exiting the speaker at an angle of about 65 degrees with respect to the speaker axis 1116. The straight audio port 1122 is positioned on the outer surface 1114 of the speaker cover generally in line with the speaker axis 1116.

Figure 44:
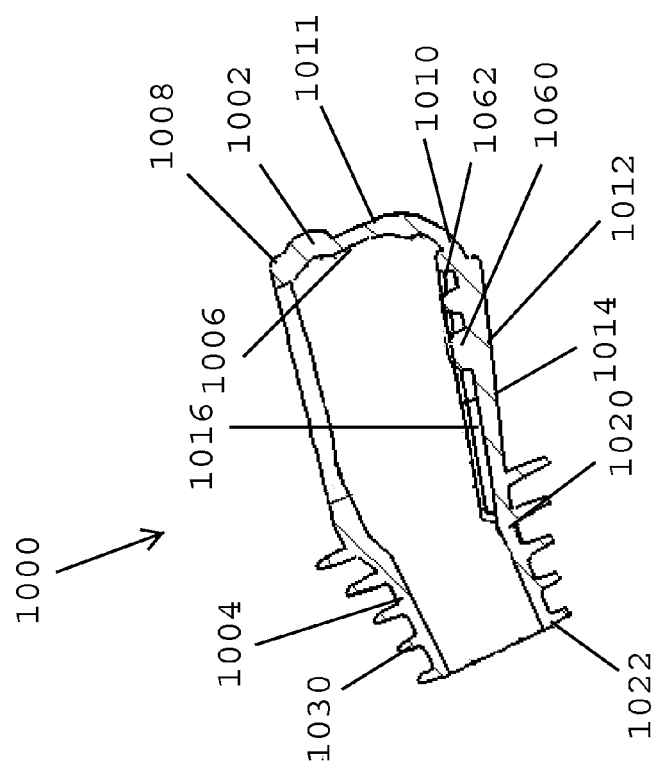
FIG. 44 is a cross sectional view of an earpod style adapter taken along line B-B in FIG. 39.

The adapter 1000 generally includes a sleeve portion 1002 and an ear portion 1004. As shown in FIGS. 33 through 44, in one embodiment, the sleeve portion 1002 is a generally annular sleeve that includes an inner surface 1006 having a diameter that is sized to fit over the outside of the sidewall 1111 of the earpod 1100. Similar to the first embodiment, the inner surface 1006 is sized to press fit over the outside diameter of the earpod 1100 for a secure fit. As shown in FIG. 44, in one embodiment, the sleeve portion 1002 includes a first end 1008, a second end 1010 opposite the first end 1008, and a sidewall 1011 extending therebetween. As illustrated, the second end 1010 is closed by a face 1012, which includes an exterior surface 1014 and an interior surface 1016. When attached to the earpod 1100, the interior surface 1016 of the face 1012 may contact the outer surface 1114 of the speaker cover 1112.

In addition, the sleeve portion 1002 may include a bulbous edge 1018 similar to the bulbous edge 34 described above to further enhance the tight fit of the sleeve portion 1002 on the earpod 1100. However, in this embodiment, the bulbous portion may extend at an angle across the sleeve portion 1002. As noted above, the bulbous edge 1018 reduces the stretch in the first end 1008 of the sleeve portion 1002 to prevent the sleeve 1002 from being pulled off the earpod during activity. The size, shape and configuration of the sleeve portion 1002 may vary from application to application in part to accommodate the desired earpods. The resulting improved pull off from this arrangement allows the adapter 1000 to be molded from extremely soft elastomeric materials for improved comfort and still stay attached on the earpod 1100. For instance, silicone rubber between 5 to 20 shore A hardness could be used. In one embodiment, the sleeve portion 1002 may be formed with dimensions smaller than those of the earpod 1000 so that the sleeve portion 1002 is stretched onto the earpod 1000, which results in the sleeve portion 1002 gripping the earpod 1000.

Figure 43:
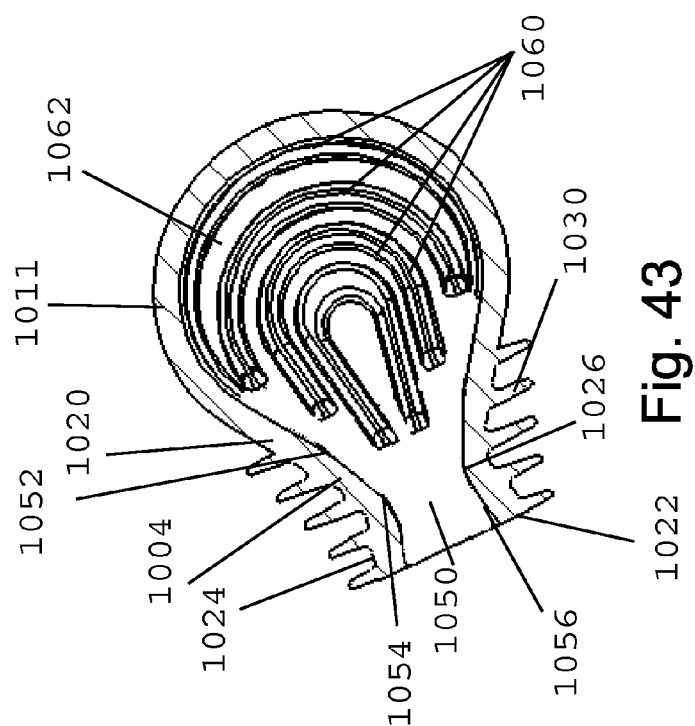
FIG. 43 is a cross sectional view of an earpod style adapter taken along line A-A in FIG. 40.

Referring to FIGS. 43 and 44, the interior surface 1016 of the face 1012 may include one or more projections 1060 extending outwardly from the surface 1016. The projections 1060 engage the outer surface 1114 of the speaker cover 1112 to hold at least portions of the surface 1016 at a standoff from the speaker cover 1112 and enable the travel of sound waves through gaps between the surface 1016 and the speaker cover 1112. As shown in FIG. 43, the projections 1060 may define channels 1062 therebetween for directing the sound waves towards the ear portion 1004, which is described in more detail below. More particularly, the projections 1060 may include a series of C-shaped projections 1060, sequentially nested inside one another, forming C-shaped channels 1062 that are positioned to open toward the ear portion 1004. In this manner, sound waves exiting the straight audio port 1122 are re-directed through the channels and toward the ear portion 1004.

As illustrated, the earpod adapter 1000 includes an ear portion 1004 extending from the sleeve portion 1002. In this configuration, the ear portion 1004 extends from the sidewall 1011 of the sleeve 1002 such that the ear portion 1004 is generally in alignment with the angled audio port 1120 on the earpod 1000. The ear portion 1004 is a tubular projection having a first end 1020 attached to the sidewall 1011 of the sleeve portion 1002 and a second end 1022 opposite the first end. The ear portion 1002 has an outer surface 1024 and an inner surface 1026 opposite the outer surface 1024. The inner surface 1026 defines an opening or channel 1050 for transmission of sound from the speaker 1101 through the adapter 1000. The ear portion 1004 may be formed integrally with the sleeve portion 1002, for instance, by injection molding. Similar to the first embodiment, the ear portion 1004 and the ear portion channel 1050 extends at an angle with respect to the speaker axis 1116. In one embodiment, shown in FIGS. 35-38, the ear portion 1004 defines a port axis 1029 that is angled about 65 degrees from the speaker axis (see, in particular, FIG. 35), although the adapter 1000 may be constructed with a different angle between the sleeve portion 1002 and the ear portion 1004. The angle between the speaker axis 1116 and the port axis 1029 defined by the ear portion 1002 enables the adapter 1000 to fit comfortably within the user's ear while also redirecting sound from the speaker in a path that is more generally aligned with the user's ear canal. In one embodiment, the thickness of the ear portion 1002 is between about 1 mm to 3 mm. In the embodiment shown in FIGS. 33-44, the outer surface 1024 of the ear portion 1004 is shaped to generally follow the shape of the inner surface 1026, which may be a twin cone shape along at least one plane. For example, in the illustrated embodiment, the twin cone shape is formed at least in the plane shown in FIG. 43, but the twin cone shape is not formed in all planes including the plane shown in FIG. 44.

In one embodiment, a plurality of fins 1030 extend from the outer surface 1024. The fins 1030 are generally the same as the fins 22 described in connection with the first embodiment, and thus will not be described again in detail. Suffice it to say that the flexible fins conform and adapt to the interior surface of the user's ear canal to prevent unwanted removal from the ear and to seal against the surface of the ear canal to prevent sound loss and thus provide higher sound quality.

As further shown in FIGS. 43 and 44, the interior surface 1026 of the ear portion 1004 may have a twin cone air channel 1050. The twin cone air channel 1050 is similar to that of the first embodiment, and thus will not be described again in great detail. Suffice it to say that the air channel 1050 generally includes a converging cone 1052, a transition portion 1054 and a diverging cone 1056. In this embodiment, the twin cone air channel 1050 extends in at least one plane. The illustrated twin cone air channel 1050 provides improved sound quality at least in part because the smooth curves in the interior surface 1026 of the ear portion reduce or eliminate abrupt changes in the cross-sectional area of the air channel 1050.

FIGS. 45-56 show another embodiment of the present invention wherein an earpod style earphone is integrated with a flexible in-ear adapter to form a standalone earphone 2000. FIGS. 45-47 shown exploded views of the earphone 2000, which generally includes an earpod portion 2100 and an in-ear portion 2010. The earpod portion 2100 is similar to the earpod 1100 described above, having a speaker housing 2110 with a sidewall 2111 that terminates in a rim 2113 that is generally flush with the speaker 2101. The speaker may have a movable central portion 2103 that defines a speaker face, and a perimeter 2104. In this embodiment, the speaker cover 2112 is mounted to the rim 2113 of the sidewall 2111 in such a manner that the speaker cover 2112 can swivel with respect to the sidewall 2111 in the direction shown by the arrow in FIG. 48. For example, a rail 2200 on the interior of the speaker cover 2112 may snap fit or otherwise interfit with a rail 2202 on the rim 2113 of the housing sidewall 2111. In one embodiment, this connection enables the speaker cover 2112 to swivel 360 degrees with respect to the speaker housing 2111 in a plane generally defined by the rim 2113 of the speaker housing 2111. The ability of the speaker cover 2112 to swivel with respect to the speaker housing 2111 creates a more user friendly experience as the user can rotate the speaker cover 2112 and the in-ear portion 2010 to position the in-ear portion in the user's ear with the speaker housing 2111 and cord in the most comfortable position for the user.

In one embodiment, the speaker cover 2112 is dome shaped, and includes an outer surface 2114 and a peripheral edge 2115 forming a rim adjoined to the rim 2113 of the sidewall 2111. The speaker cover 2112 may be formed of a rigid piece of plastic or other material, and may include a port or ports that direct the passage of sound. In the illustrated embodiment, the speaker cover 2112 includes an angled audio port 2120 positioned in the speaker cover 2112 adjacent to the peripheral edge 2115. As illustrated, the angled audio port 2120 is positioned to redirect sound exiting the speaker at an angle of about 65 degrees with respect to the speaker axis 2116. Other audio ports may be included as desired.

Figure 50:
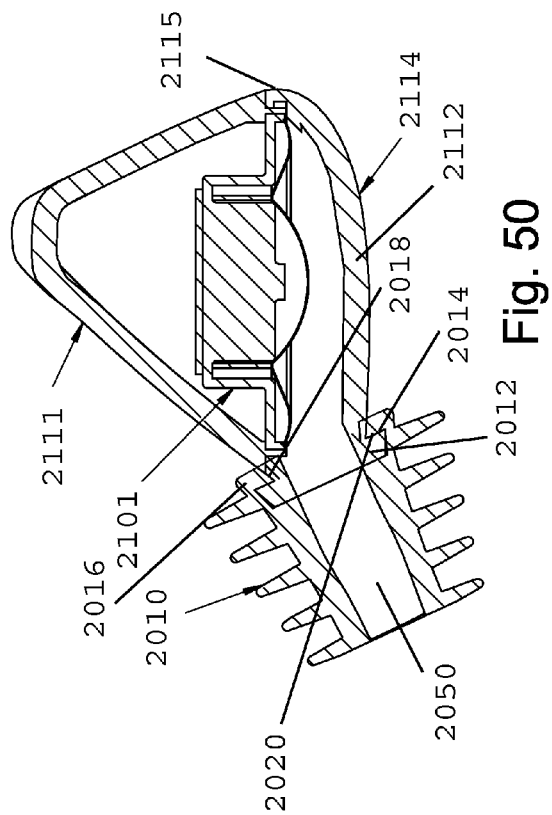
FIG. 50 is a cross sectional view taken along line B-B in FIG. 49.
Figure 49:
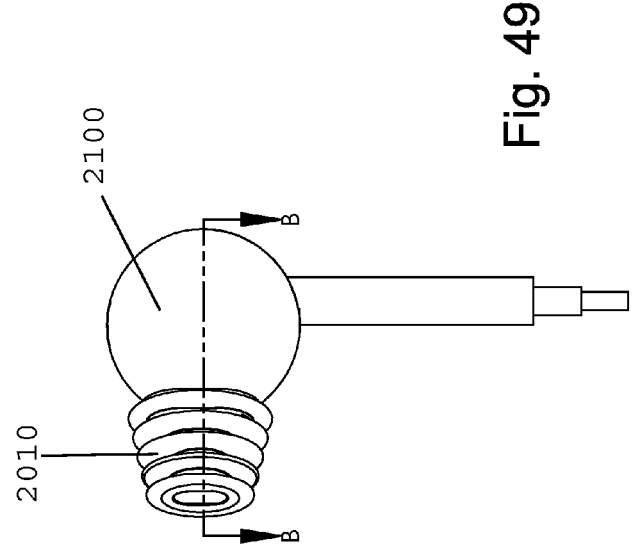
FIG. 49 is another front view thereof.
Figure 51:
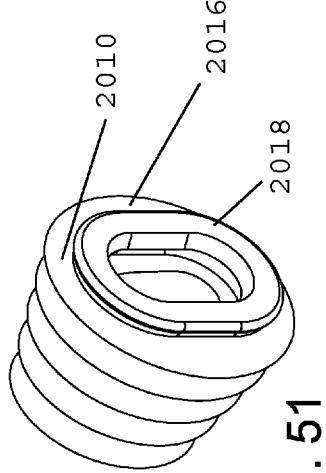
FIG. 51 is a rear view of an ear portion of the earpod style earphone.
Figure 52:
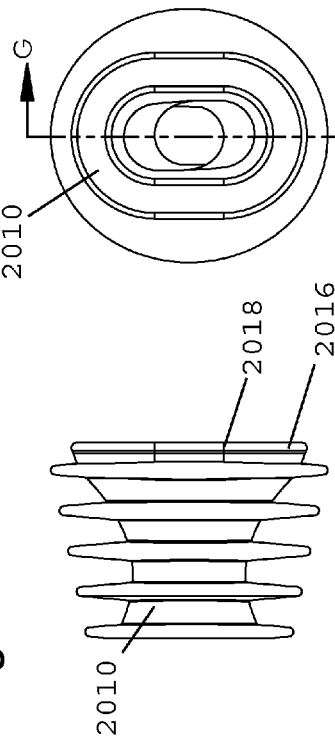
FIG. 52 is a side view thereof.
Figure 53:
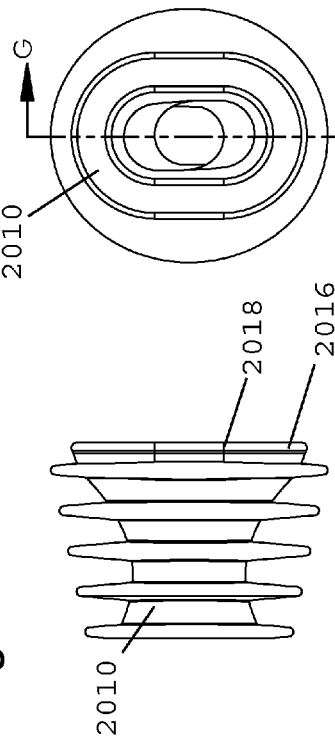
FIG. 53 is a front view thereof.
Figure 54:
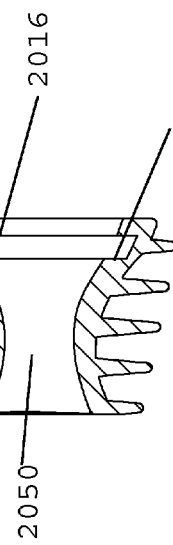
FIG. 54 is another front view thereof.
Figure 55:
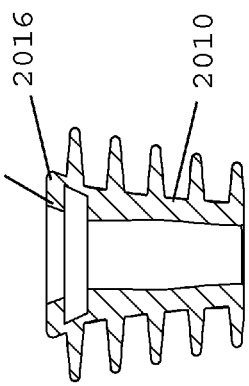
FIG. 55 is a cross sectional view taken along line E-E in FIG. 54.
Figure 56:
FIG. 56 is a cross sectional view taken along line G-G in FIG. 53.

The in-ear portion 2010 is similar to the adapter 1000 described above, and therefore will not be described in detail. However, the in-ear portion 2010 may be designed for a more permanent connection to the speaker cover 2112. As shown in FIG. 50, in one embodiment, the speaker cover 2112 includes an upstanding rim 2012 extending from the speaker cover 2112 around the angled audio port 2120. The rim 2012 may project radially outwardly from the speaker cover 2112 to form an exposed rear surface 2014. The in-ear portion 2010 may include corresponding structure for mating with the rim 2012 of the speaker cover 2112. In the illustrated embodiment, the in-ear portion includes a first end 2016 with an undercut ring 2018 having a rear surface 2020. The undercut ring 2018 may be attached over the rim 2012 of the speaker cover 2112 such that the rear surface 2014 of the rim 2012 engages the rear surface 2020 of the undercut ring 2018 to retain the in-ear portion 2010 on the speaker cover 2112. In a manner similar to the earpod 1100 and adapter 1000 described above, the angled audio port 2120 and the tubular inner channel 2050 of the in-ear portion 2010 cooperate to redirect sound waves exiting the speaker at an angle with respect to the speaker axis. This angle may be varied as desired for comfort and sound. The gradually sloping, continuously curving nature of the cone shapes within the sound channel 2050 act to maintain the sound quality of the speaker as the sound is redirected. An alternative embodiment of the standalone device is shown in FIGS. 57 and 58. This embodiment depicts a Bluetooth earpiece 3000 having a speaker cover 3112, speaker 3101, speaker housing 3111 and Bluetooth receiver and microphone 3001. An in-ear portion 3110, which is substantially the same as the in-ear portion 2010, may attach to the speaker cover 3112 in substantially the same manner as the speaker cover 2112. Similarly, the speaker cover 3112 may attach to the speaker housing 3111 in the same manner as the speaker cover 2112 and housing 2111 described above, such that the in-ear portion can rotate with respect to the Bluetooth receiver and microphone 3001. This construction would allow the user to angle the speaker housing 3111 to achieve a preferred microphone position.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The embodiments of the invention in which an exclusive property of privilege is claimed are defined as follows:

1. An earphone system comprising:
  an earphone including a speaker housing, a speaker having a speaker face, said speaker directing sound waves emitting from said speaker in a first direction aligned along a speaker axis that is generally perpendicular to said speaker face, and a speaker cover extending over the speaker and defining an angled audio port; and
  an adapter formed from a soft, flexible material, said adapter including an attachment portion and an ear portion formed integrally as a single piece, said attachment portion including a sleeve having a first end fitted over at least a portion of said earphone and a second end opposite said first end, said ear portion including a first end extending from said attachment portion and a second end opposite said first end, said ear portion including an exposed outer surface of the soft, flexible material in direct contact with an interior surface of a user's ear canal and shaped to conform to the user's ear canal, and an inner surface opposite said outer surface and defining an internal opening extending through said ear portion from said first end to said second end, said internal opening forming an air channel for directing sound from said speaker through said ear portion, said air channel having at least a portion extending along a port axis oriented at an angle with respect to said speaker axis such that said adapter redirects the portion of sound waves traveling along said speaker axis to travel along said port axis.

2. The earphone system of claim 1 wherein said port axis is oriented at an angle between about 45 and 90 degrees from said speaker axis.

3. The earphone system of claim 2 wherein said port axis is oriented at an angle of about 65 degrees from said speaker axis.

4. The earphone system of claim 1 wherein said inner surface of said ear portion includes at least one of a converging cone shape and a diverging cone shape.

5. The earphone system of claim 4 wherein said inner surface of said ear portion defines a width that is perpendicular to the longitudinal extent of said ear portion, wherein said width is continuously changing from said first end to said second end of said ear portion.

6. The earphone system of claim 5 wherein said inner surface of said ear portion has a twin cone shape, wherein said interior opening includes a first portion having a width that decreases extending away from said first end of said ear portion, and a second portion having a width that increases approaching said second end of said ear portion.

7. The earphone system of claim 6 including a plurality of flexible fins extending outwardly from said outer surface of said ear portion, said fins spaced apart between said first and second ends of said ear portion.

8. The earbud adapter of claim 7 wherein said fins extend continuously around the circumference of said ear portion.

9. The earbud adapter of claim 8 wherein said piece is an elastomer having a durometer of less than 70 Shore A.

10. The earphone system of claim 2 wherein said speaker is positioned between said speaker cover and said speaker housing, said speaker cover formed from rigid plastic and defining the angled audio port and a straight audio port.

11. The earphone system of claim 10 wherein said speaker cover includes a peripheral edge attached to said speaker housing, said angled audio port positioned adjacent said peripheral edge, said straight audio port spaced from said angled audio port.

12. The earphone system of claim 11 wherein said attachment portion includes a sidewall extending between said first end and said second end of said sleeve, and an end wall at said second end, said wall closing said sleeve at said second end.

13. The earphone system of claim 12 wherein said ear portion extends from said sidewall.

14. The earphone system of claim 13 wherein said end wall includes an interior surface facing said speaker cover and an exterior surface opposite said interior surface.

15. The earphone system of claim 14 wherein said interior surface of said end wall includes at least one projection extending outwardly from said interior surface to engage said speaker cover and hold said interior surface at a standoff from said speaker cover.

16. The earphone system of claim 15 wherein said at least one projection includes a plurality of projections forming channels therebetween, said channels directing sound waves toward said ear portion.

17. The earphone system of claim 16 wherein said plurality of projections include a series of nested, C-shaped projections.

18. An adapter for attaching to an earpod style earphone having a speaker, a speaker cover extending over the speaker and an angled audio port defined in the speaker cover, the adapter comprising:
  a resilient, flexible sleeve adapted to extend over a portion of the earpod to attach the adapter to the earpod, said sleeve including an open end for fitting over the earpod, a closed end opposite said open end, and a sidewall extending between the open end and the closed end, the closed end including an interior surface and an exterior surface, said interior surface including a plurality of projections extending outwardly therefrom for holding said interior surface at a standoff from the speaker cover when the adapter is attached to the earpod; and
  a tubular ear portion extending from said sidewall of said sleeve, said ear portion including a first end proximate said sleeve such that said first end is capable of aligning with said angled audio port when the adapter is attached to the earpod, a second end opposite said first end, and an inner surface defining an opening extending through said ear portion from said first end to said second end, wherein the plurality of projections form channels therebetween that direct sound waves toward the ear portion.

19. The adapter of claim 18 wherein said plurality of projections include a series of nested, C-shaped projections.

20. The adapter of claim 19 wherein said inner surface includes a width defined generally perpendicular to the longitudinal extent of the ear portion, said inner surface including a first portion having a width that decreases extending away from said first end and a second portion having a width that increases approaching said second end.

21. The adapter of claim 20 wherein said ear portion includes an outer surface opposite said inner surface, and a plurality of fins extending outwardly from said outer surface.

22. The earphone system of claim 1 further comprising at least one rib element on the outer surface of the ear portion.

23. The earphone system of claim 22 wherein the at least one rib element comprises a plurality of flexible fins extending outwardly from said outer surface of said ear portion.

24. The earphone system of claim 1 wherein said adapter is made from an elastomer having a durometer of less than 70 Shore A.

25. An adapter for attaching to an earphone having a speaker housing and a speaker having a speaker face, said speaker directing sound waves emitting from said speaker in at least a first direction aligned along a speaker axis that is generally perpendicular to said speaker face, the adapter comprising:

a resilient, flexible sleeve adapted to extend over at least a portion of the earphone to attach the adapter to the earphone, said sleeve including an open end for fitting over the earphone, a closed end opposite said open end, and a sidewall extending between the open end and the closed end, the closed end including an interior surface and an exterior surface; and a tubular ear portion extending from said sidewall of said sleeve, said ear portion including a first end proximate said sleeve, a second end opposite said first end, an inner surface defining an opening extending through said ear portion from said first end to said second end, and an outer surface opposite the inner surface and comprising at least one rib element extending outwardly from at least a portion of said outer surface to increase at least one of retention or sound isolation of the earphone, wherein the sleeve and the ear portion are formed integrally as a single piece, and wherein said interior surface of the ear portion includes at least one projection extending outwardly therefrom for holding said interior surface at a standoff from the speaker cover when the adapter is attached to the earphone, the at least one projection forming at least one channel for directing sound waves emitted by the speaker to the opening formed in the ear portion.

* * * * *